(12) United States Patent
VanEvery et al.

(10) Patent No.: US 12,721,695 B2
(45) Date of Patent: Sep. 1, 2026

(54) STABILIZER SYSTEMS FOR MEDICAL PROCEDURES THAT MAINTAIN STERILITY OF AN ARTICULATING ARM ABOVE A STERILE BARRIER

(71) Applicant: EDWARDS LIFESCIENCES CORPORATION, Irvine, CA (US)

(72) Inventors: Zachary Charles VanEvery, Irvine, CA (US); Linda Thai, Mission Viejo, CA (US); Daniel James Murray, Orange, CA (US); Max Alexander Cruzan, Irvine, CA (US); Jonathan Andrew Lam, Anaheim Hills, CA (US); Ajay Kumar Dass, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 82 days.

(21) Appl. No.: 18/813,449

(22) Filed: Aug. 23, 2024

(65) Prior Publication Data

US 2024/0407885 A1 Dec. 12, 2024

Related U.S. Application Data

(63) Continuation of application No. PCT/US2023/014390, filed on Mar. 2, 2023.

(Continued)

(51) Int. Cl.
*A61B 90/57* (2016.01)

(52) U.S. Cl.
CPC ........ *A61B 90/57* (2016.02); *A61B 2090/571* (2016.02)

(58) Field of Classification Search
CPC .......................... A61B 90/57; A61B 2090/571
(Continued)

(56) References Cited

U.S. PATENT DOCUMENTS 2,963,247 A * 12/1960 Collier .............. A61M 16/0672 604/23
3,530,515 A * 9/1970 Jacoby ................ A61G 7/0501 128/200.24

(Continued)

FOREIGN PATENT DOCUMENTS

DE 10124490 A1 11/2002
EP 0752237 A1 1/1997

(Continued)

*Primary Examiner* — Anita M King
(74) *Attorney, Agent, or Firm* — Chang and Hale LLP

(57) ABSTRACT

Disclosed herein are stabilizer systems that include a base for securing the stabilizer system to a patient table by inserting the base between the patient table and the mattress on the patient table. The stabilizer systems also include a connector that connects a lockable articulating arm to the base. The base protrudes from under the mattress slightly to provide a sturdy and predictable surface to attach the articulating arm of the stabilizer system. The base can then be used to support a lockable articulating arm with a clamp at its distal end for holding an access sheath or delivery system. The connectors attach the articulating arm to the base so that the articulating arm is above the sterile surgical drape to maintain sterility of the articulating arm. The stabilizer systems are advantageous in jugular access procedures.

19 Claims, 21 Drawing Sheets

Related U.S. Application Data

(60) Provisional application No. 63/317,944, filed on Mar. 8, 2022.

(58) Field of Classification Search
USPC ........ 248/121; 128/200.24, 204, 18, 205.26; 5/503.1, 658
See application file for complete search history.

(56) References Cited

U.S. PATENT DOCUMENTS

| | | | | |
|---|---|---|---|---|
| 3,859,993 | A * | 1/1975 | Bitner | A61M 16/009 5/507.1 |
| 4,321,917 | A * | 3/1982 | Campbell | A61G 13/107 5/503.1 |
| 4,971,037 | A * | 11/1990 | Pelta | A61B 90/50 600/230 |
| 5,704,900 | A * | 1/1998 | Dobrovolny | A61B 17/0281 600/235 |
| 6,151,734 | A * | 11/2000 | Lawrie | A47C 20/026 5/643 |
| 6,471,172 | B1 | 10/2002 | Lemke et al. | |
| 6,626,408 | B1 * | 9/2003 | Lorbiecki | A61B 6/0421 248/279.1 |
| 7,886,743 | B2 | 2/2011 | Cooper et al. | |
| 8,105,338 | B2 | 1/2012 | Anderson et al. | |
| 8,640,706 | B2 | 2/2014 | Skora et al. | |
| 10,357,324 | B2 | 7/2019 | Flatt et al. | |
| 10,456,208 | B2 | 10/2019 | Thompson et al. | |
| 2010/0268250 | A1 | 10/2010 | Stuart et al. | |
| 2015/0202009 | A1 | 7/2015 | Nussbaumer et al. | |
| 2018/0000472 | A1 | 1/2018 | Beira | |
| 2018/0125597 | A1 | 5/2018 | Gogarty et al. | |
| 2019/0000580 | A1 | 1/2019 | Scheib et al. | |
| 2020/0069383 | A1 | 3/2020 | Betsugi et al. | |
| 2020/0170724 | A1 | 6/2020 | Flatt et al. | |
| 2020/0230362 | A1 | 7/2020 | Basude | |
| 2021/0137635 | A1 | 5/2021 | Gomez et al. | |

FOREIGN PATENT DOCUMENTS

| | | | |
|---|---|---|---|
| JP | 6427253 | B1 | 11/2018 |
| WO | 2013075205 | A1 | 5/2013 |

* cited by examiner 154
152
100
130
120
140
110
156

131
132
134
135
136
133
130
112

STABILIZER SYSTEMS FOR MEDICAL PROCEDURES THAT MAINTAIN STERILITY OF AN ARTICULATING ARM ABOVE A STERILE BARRIER

CROSS-REFERENCE TO RELATED APPLICATION

This application is a continuation of International Patent Application No. PCT/US2023/014390, filed Mar. 2, 2023 and entitled STABILIZER SYSTEMS FOR MEDICAL PROCEDURES THAT MAINTAIN STERILITY OF AN ARTICULATING ARM ABOVE A STERILE BARRIER, which claims priority to U.S. Prov. App. No. 63/317,944 filed Mar. 8, 2022 and entitled STABILIZER SYSTEMS FOR MEDICAL PROCEDURES THAT MAINTAIN STERILITY OF AN ARTICULATING ARM ABOVE A STERILE BARRIER, the complete disclosures of which are hereby incorporated by reference in their entireties.

BACKGROUND

Field

The present disclosure relates to the field of stabilizer systems for use with medical devices and procedures.

Description of Related Art

Various medical procedures include the introduction of a transcatheter medical device into a patient and require controlled use of the catheter. It is advantageous to secure the medical device during the procedure in a way that allows the device to be held stationary during portions of the procedure and to be adjusted during other portions of the procedure. This can be accomplished using a stabilizer system.

These medical procedures can be performed in a specialized lab, such as a catheterization lab. These specialized labs can include a bed or table where a patient lies during the procedure. Typically, there is a lot of equipment and many people present during these procedures and space can be at a premium around the table. A stabilizer system can be positioned at the table to allow the stabilizer system to secure the medical device near the patient.

SUMMARY

Described herein are one or more systems or devices to hold a medical device (e.g., a catheter) during a medical procedure in a way that maintains sterility of an articulating arm above a sterile barrier. The systems and devices include a base with a connector interface that enables a connector to connect to the base with a sterile barrier (e.g., a sterile surgical drape) pressed between the connector and the base. This enables sterility of the connector to be maintained during connection of the connector to the base.

In some implementations, the sterile barrier forms a non-sterile region that includes the base and forms a sterile region that includes the connector. In some implementations, an articulating arm can be coupled to the connector so that the articulating arm is in the sterile region.

In some implementations, the techniques described herein relate to a stabilizer system for use in a medical procedure to stabilize an access sheath or a delivery device. The stabilizer system includes a base configured to be positioned between a patient table and a pad on the patient table. The stabilizer system also includes an articulating arm. The stabilizer system also includes a connector configured to secure the articulating arm to a portion of the base that protrudes from under the pad. The stabilizer system also includes a holder at a distal end of the articulating arm, the holder configured to interface with the access sheath or delivery device. The connector is configured to connect to the base in a way that maintains sterility of the articulating arm above a sterile barrier during connection of the connector to the base.

In some implementations, the techniques described herein relate to a stabilizer system, wherein the base includes a stabilizing portion and a protruding portion separated by a wall that extends vertically from the base.

In some implementations, the techniques described herein relate to a stabilizer system, wherein the portion of the base that protrudes from under the mattress or pad forms a base mounting portion that mates with the connector.

In some implementations, the techniques described herein relate to a stabilizer system, wherein the connector includes an arm mating pin configured to mate with the articulating arm.

In some implementations, the techniques described herein relate to a stabilizer system, wherein the connector includes a shaft, a tapered clamp plate, and a bottom clamp plate.

In some implementations, the techniques described herein relate to a stabilizer system, wherein the tapered clamp plate has an oblong cross-section.

In some implementations, the techniques described herein relate to a stabilizer system, wherein the base forms a base mounting portion with an oblong shape complementary to the oblong cross-section of the tapered clamp plate.

In some implementations, the techniques described herein relate to a stabilizer system, wherein the base forms a base mounting portion that is tapered to complement a taper of the tapered clamp plate.

In some implementations, the techniques described herein relate to a stabilizer system, wherein the connector further includes an internally threaded knob that mates with a threaded portion of the shaft, the tapered clamp plate secured to the internally threaded knob.

In some implementations, the techniques described herein relate to a stabilizer system, wherein the bottom clamp plate is axially locked to the shaft and is free to rotate around the shaft.

In some implementations, the techniques described herein relate to a stabilizer system, wherein the connector connects to the base by applying a clamping force on the base between the tapered clamp plate and the bottom clamp plate.

In some implementations, the techniques described herein relate to a stabilizer system, wherein a portion of the shaft has an oblong cross-section and the tapered clamp plate is internally keyed to the oblong cross-section of the portion of the shaft.

In some implementations, the techniques described herein relate to a stabilizer system, wherein the base forms a base mounting portion on the portion of the base that protrudes from under the mattress or pad.

In some implementations, the techniques described herein relate to a stabilizer system, wherein a surgical drape is configured to lie between the base mounting portion and the connector upon connecting the connector to the base.

In some implementations, the techniques described herein relate to a stabilizer system, wherein the base mounting portion includes a different material from the rest of the base.

In some implementations, the techniques described herein relate to a stabilizer system, wherein the base is radiolucent.

In some implementations, the techniques described herein relate to a stabilizer system, wherein the holder includes a lever-actuated clamp with pre-tensioned springs to form a two-stage clamping mechanism.

In some implementations, the techniques described herein relate to a stabilizer system, wherein the articulating arm includes a vertical post that is held vertically stable in relation to the connector during a medical procedure.

In some implementations, the techniques described herein relate to a stabilizer system, wherein the holder is releasably attached to the articulating arm.

In some implementations, the techniques described herein relate to a stabilizer system, wherein the articulating arm is releasably attached to the connector.

In some implementations, the techniques described herein relate to a stabilizer system including: a base including a stabilizing portion and a protruding portion, the stabilizing portion configured to be inserted between a mattress and a table such that the protruding portion extends outward from between the mattress and the table, the protruding portion forming a base mounting portion; and a connector including a shaft, a top plate, and a bottom plate, the top plate and the bottom plate configured to approximate to each other along an axial direction of the shaft, wherein the connector is configured to mate with the base mounting portion to secure the connector to the base with a surgical drape pressed between the connector and the base, the top plate and the bottom plate configured to apply a clamping force on the base mounting portion to secure the connector to the base.

In some implementations, the techniques described herein relate to a stabilizer system further including a knob coupled to the top plate, wherein rotation of the knob causes the top plate and the bottom plate to axially approximate.

In some implementations, the techniques described herein relate to a stabilizer system, wherein the connector further includes a grooved ring assembly to secure the knob to the top plate such that rotation of the knob causes the top plate to translate axially along the shaft toward the bottom plate.

In some implementations, the techniques described herein relate to a stabilizer system, wherein the top plate is internally keyed to a cross-section of the shaft to prohibit rotation of the top plate relative to the shaft.

In some implementations, the techniques described herein relate to a stabilizer system, wherein the top plate has an oblong horizontal cross-section that is complementary to an oblong horizontal cross-section of the base mounting portion to resist rotation of the top plate relative to the base mounting portion.

In some implementations, the techniques described herein relate to a stabilizer system, wherein the top plate has a tapered vertical cross-section that is complementary to a tapered vertical cross-section of the base mounting portion to enable secure connection between the connector and the base with a surgical drape of an unknown thickness between the connector and the base.

In some implementations, the techniques described herein relate to a stabilizer system, wherein the bottom plate is secured to the shaft so that the bottom plate is axially fixed relative to the shaft but is free to rotate around the shaft.

In some implementations, the techniques described herein relate to a stabilizer system, wherein the base mounting portion forms an opening with a horseshoe shape.

In some implementations, the techniques described herein relate to a stabilizer system, wherein a horizontal cross-section of the top plate forms a pill shape.

In some implementations, the techniques described herein relate to a stabilizer system, wherein the connector further includes an arm mating pin configured to secure an articulating arm to the connector.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1A:
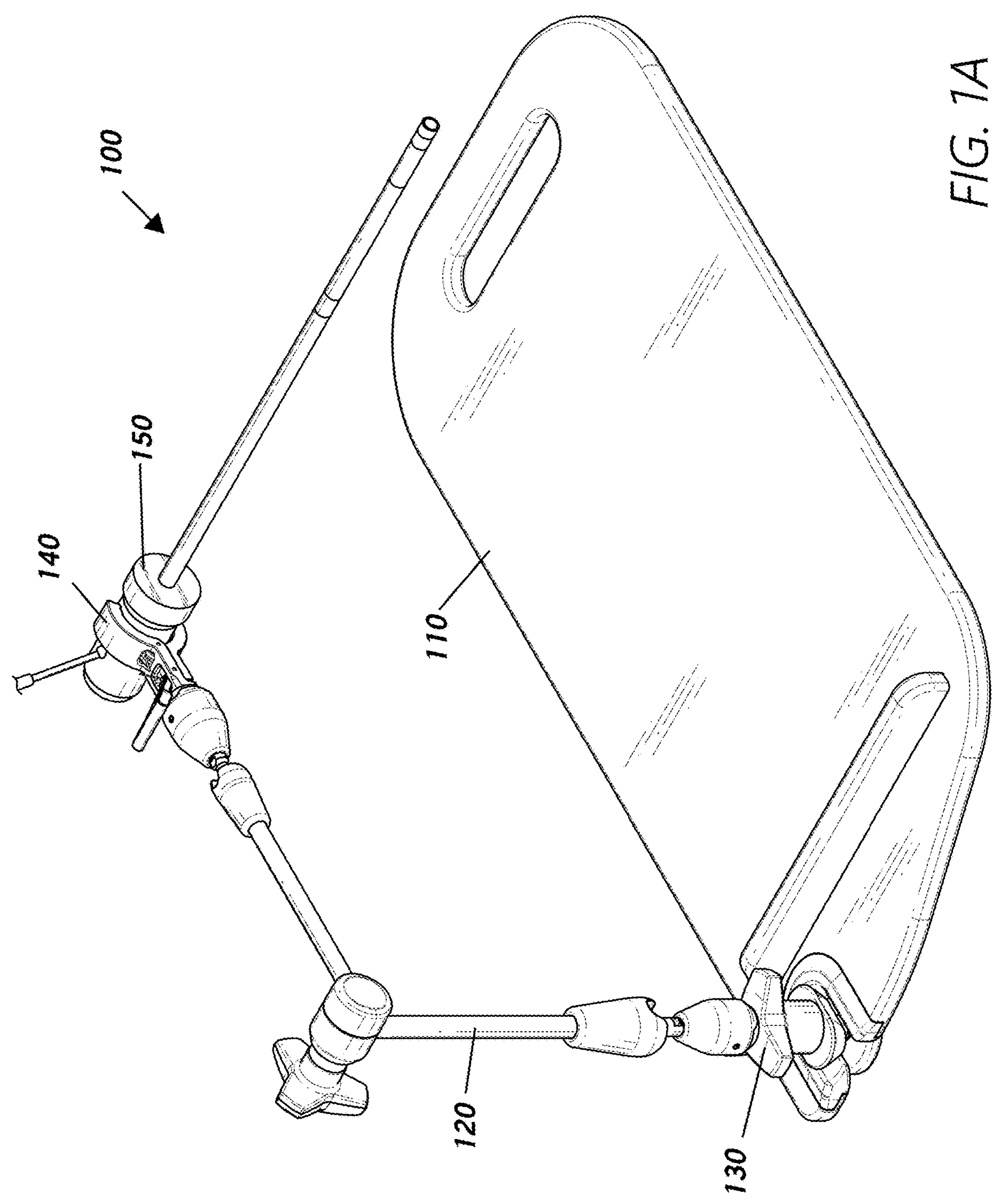
FIGS. 1A, 1B, and 1C illustrate examples of a stabilizer system for use in medical procedures to secure an access sheath or delivery device.

The headings provided herein are for convenience only and do not necessarily affect the scope or meaning of the claimed subject matter. The present disclosure relates to systems, devices, and methods to provide stabilization for medical devices while maintaining a sterile barrier between a base and an articulating arm that holds the medical device (e.g., an access sheath or a delivery device such as a catheter).

Various medical procedures require the controlled use of medical devices (e.g., an access sheath or delivery device such as a catheter). Typically, during such a medical procedure, a portion of a medical device must be positioned near a patient's body or near a surgical site during the medical procedure. Often, during such procedures, the medical device must be manipulated and repositioned. On the other hand, inadvertent movement or unintended positioning of the medical device during a delicate medical procedure is undesirable and can be dangerous to the patient, particularly when there are portions of the medical device, such as a catheter or implant, that have been positioned within the body. Thus, it is desirable to stabilize the medical device during the medical procedure.

Stabilization may be provided by a person. However, it may be undesirable to use an additional person to stabilize the access sheath or delivery device because it may increase crowding at the table where the patient is positioned. During jugular access procedures, in particular, using a person to stabilize access sheaths and/or delivery devices can be difficult due to a lack of available space at the head of the table where the patient is positioned. Thus, it may be desirable to reduce the number of people required in that space during the procedure while still providing stabilization to a medical device. In addition, due to this lack of space, the person may be exposed to increased levels of radiation if fluoroscopy is required.

Stabilizer systems (e.g., mechanical stabilizers) can be used to position and secure a medical device rather than using a dedicated person to provide the same functionality. A stabilizer system holds the medical device in place relative to a patient or surgical site. This reduces the risk of inadvertent movement of the medical device. However, challenges arise with stabilizer systems due to variances in table and equipment configurations. For example, catheter lab tables are manufactured by a number of companies and there is significant variation in the design and construction of each model. This results in a less predictable secure attachment between the stabilizer system and the table. Furthermore, for certain procedures, such as jugular access procedures, there is little available footprint or space for a large stabilizer system at the head of the table. In addition, stabilizer systems may interfere with other equipment used in the medical procedure. And, with all of these stabilizer systems, a concern is the ability to easily maintain sterility of the site of the medical procedure.

Accordingly, to address these and other issues, disclosed herein are stabilizer systems that include a base for securing the stabilizer system to a patient table by inserting the base between the patient table and the mattress on the patient table. This is in contrast to stabilizer systems that attach directly to the patient table. The stabilizer systems also include a connector that connects an articulating arm to the base. The base is configured to protrude from under the mattress slightly to provide a sturdy and predictable surface to attach the articulating arm of the stabilizer system. This base can then be used to support an articulating arm. The articulating arm can have a clamp at its distal end for holding an access sheath or delivery system. The articulating arm can also be lockable. The disclosed stabilizer systems may be of particular advantage in jugular access procedures. For example, the base can be positioned under the neck/chest area of the patient with the articulating arm extending near the head and neck of the patient to secure the medical device near the jugular for jugular access procedures.

In the disclosed stabilizer systems, a connector securely attaches the articulating arm to the base. A problem that arises in connection with these and similar stabilizer systems is the manner of connecting the articulating arm to the base in a way that maintains a secure connection and provides a sterile barrier. In particular, the unpredictable geometry of sterile surgical drapes that provide the sterile barrier provides a particular challenge for connection mechanisms. Accordingly, the connector and base are configured to accommodate a variety of different configurations and geometries of the sterile surgical drape. The disclosed connectors provide a mechanical joining and/or locking of the articulating arm both torsionally and axially to the base while accommodating variable thicknesses and designs of sterile surgical drapes. The disclosed connectors are configured to attach the articulating arm to the base so that the articulating arm is above the sterile surgical drape to maintain sterility of the articulating arm. In addition, the disclosed connectors are configured to allow a person to connect the articulating arm to the base without losing sterility (e.g., without requiring the person to re-sterilize). This is accomplished using a connection mechanism with a sterile portion and a non-sterile portion, the sterile portion configured to couple to the articulating arm, the non-sterile portion configured to couple to the base. The connection mechanism is configured so that the sterile portion mates with the non-sterile portion with the sterile surgical drape at least partially between the sterile portion and the non-sterile portion.

The disclosed stabilizer systems are configured to attach to patient tables (e.g., tables in a catheterization lab) having different configurations or designs. This is enabled due to the design of the base wherein a majority of the base is positioned between the patient table and a mattress or pad on top of the patient table while a small portion of the base protrudes from under the mattress to enable connection of the articulating arm. The weight of the patient and the mattress provide stability to the stabilizer system rather than requiring a secure connection to the table itself such as to a rail on the table. The weight of the mattress (with or without the patient) and the size of the base contribute to holding the stabilizer system in place during procedures. In some embodiments, the majority of the base can be made to be radiolucent to enable fluoroscopy while the connector portion can include metal or other rigid and strong materials.

The disclosed stabilizer systems may be particularly beneficial in procedures that use steerable guide sheaths. For example, a physician may be required to maintain position both rotationally and axially once a target site has been accessed when using a steerable guide sheath. Without a stabilizer system, an additional dedicated physician may be required to be present and scrubbed in during the procedure just to hold the device in place. This may result in one or more of the following issues: lack of stability due to fatigue, loss of anatomical placement of the guide sheath due to fatigue and human error, awkward or crowded spacing at the head of the patient table, awkward interaction with insertion and removal of devices into and out of the guide sheath, and/or significant increase in radiation exposure for the physician holding the guide sheath.

The disclosed stabilizer systems provide a number of advantages while easily maintaining a sterile barrier when connecting the articulating arm to the base. For example, the disclosed stabilizer systems enable the use of a steerable, flexible guide sheath, holding the guide sheath in place near an access site on a patient. The disclosed stabilizer systems allow an operator to control depth of the access device or delivery device into the patient. The disclosed stabilizer systems allow an operator to control the torque and direction of the access sheath and/or delivery device. The disclosed stabilizer systems secure an access sheath and/or delivery device to hold it at a desired or targeted depth and in a desired or targeted orientation (wherein the orientation can be controlled with 6 degrees of freedom in some embodiments).

As another example, the disclosed stabilizer systems advantageously reduce or eliminate the risk of radiation exposure completely for the physician who would have been holding the device, lock the device both axially and rotationally to maintain position, add secure stabilization of the guide sheath to increase stability while inserting and removing other devices into the guide sheath, and reduce clutter in working area of the lab by eliminating the need for an additional physician and having a small footprint of occupied space on the table for the obtrusive portions of the stabilizer.

The disclosed stabilizer systems advantageously occupy relatively little space at the patient table. Rather than using a dedicated person to stabilize the access sheath or delivery device, the disclosed stabilizer systems provide stabilizing capabilities while reducing crowding at the patient table. Furthermore, the disclosed stabilizer systems provide little or no obstruction to other medical equipment used in the medical procedure due at least in part to the size and configuration of the articulating arm and the holder at the distal end of the articulating arm. In addition, the disclosed stabilizer systems have a relatively small footprint compared to other stabilizer systems (e.g., typical stabilizer systems for transfemoral procedures). Advantageously, the disclosed stabilizer systems provide a relatively large degree of freedom to position and orient medical devices for a medical procedure. This beneficially accommodates anatomical differences between patients, for example.

The disclosed stabilizer systems advantageously provide a secure connection to a patient table while maintaining a sterile barrier. This is accomplished without the use of rails or other mounting features on the patient table. The design of the base and connector with an articulating arm enables the disclosed stabilizer systems to be positioned where desired, such as near to a jugular access site with the articulating arm being near the patient table all while maintaining a sterile barrier. The base is placed under the mattress, the base being in a non-sterile region and providing a stable platform for secure connection of the articulating arm. The connector couples to the base in a sterile region (e.g., over a sterile surgical drape). Thus, the articulating arm can be assembled and prepared in a sterile fashion and then connected to the base (using the connector) while maintaining sterility of the articulating arm. This facilitates preparation of the medical procedure by not requiring the articulating arm to be re-sterilized when connected to the base and positioned for the medical procedure. The articulating arm can be shifted and moved to shift and move the guide sheath or delivery device during the medical procedure.

Example Stabilizer Systems

Figure 1B:
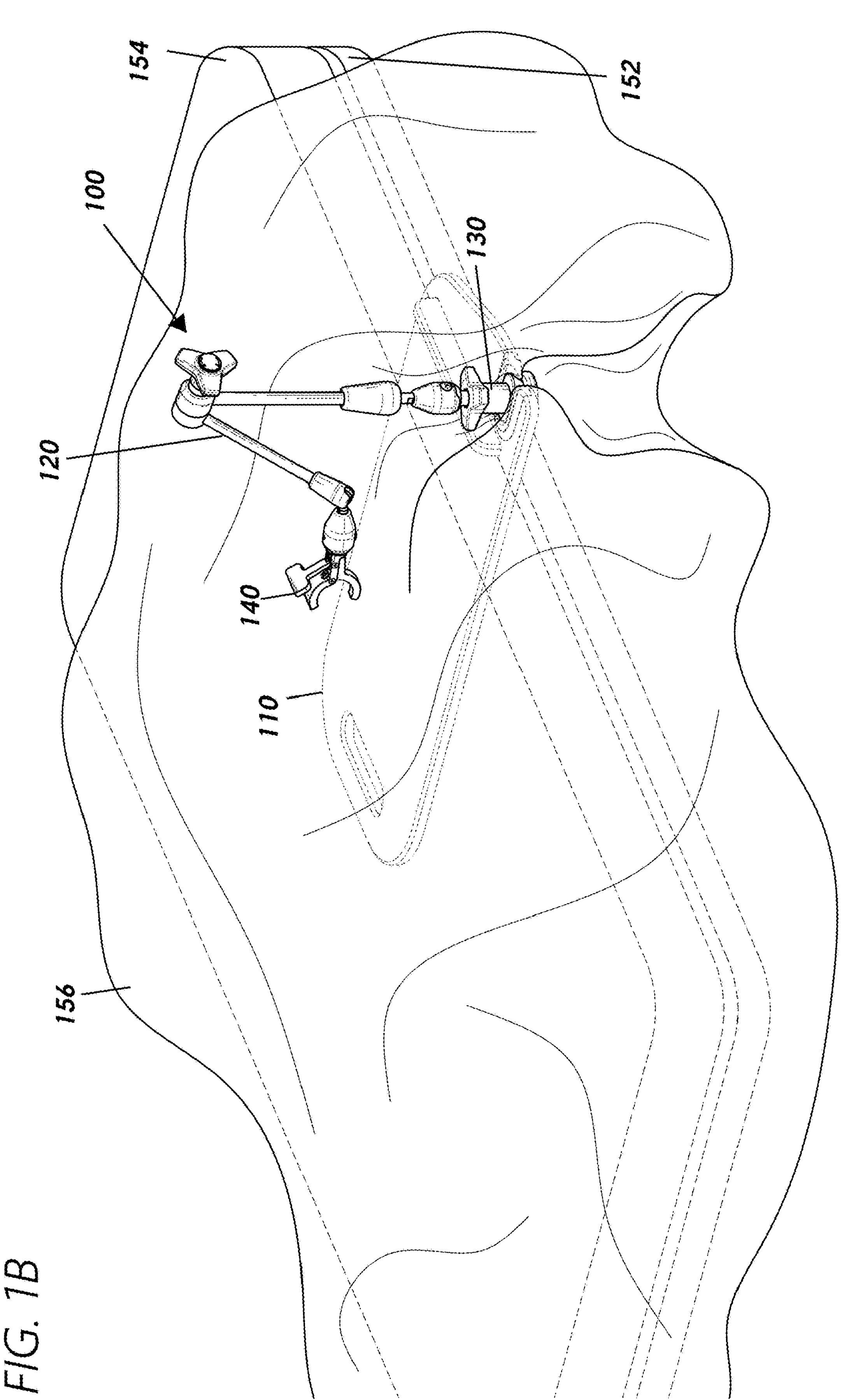
Figure 1C:
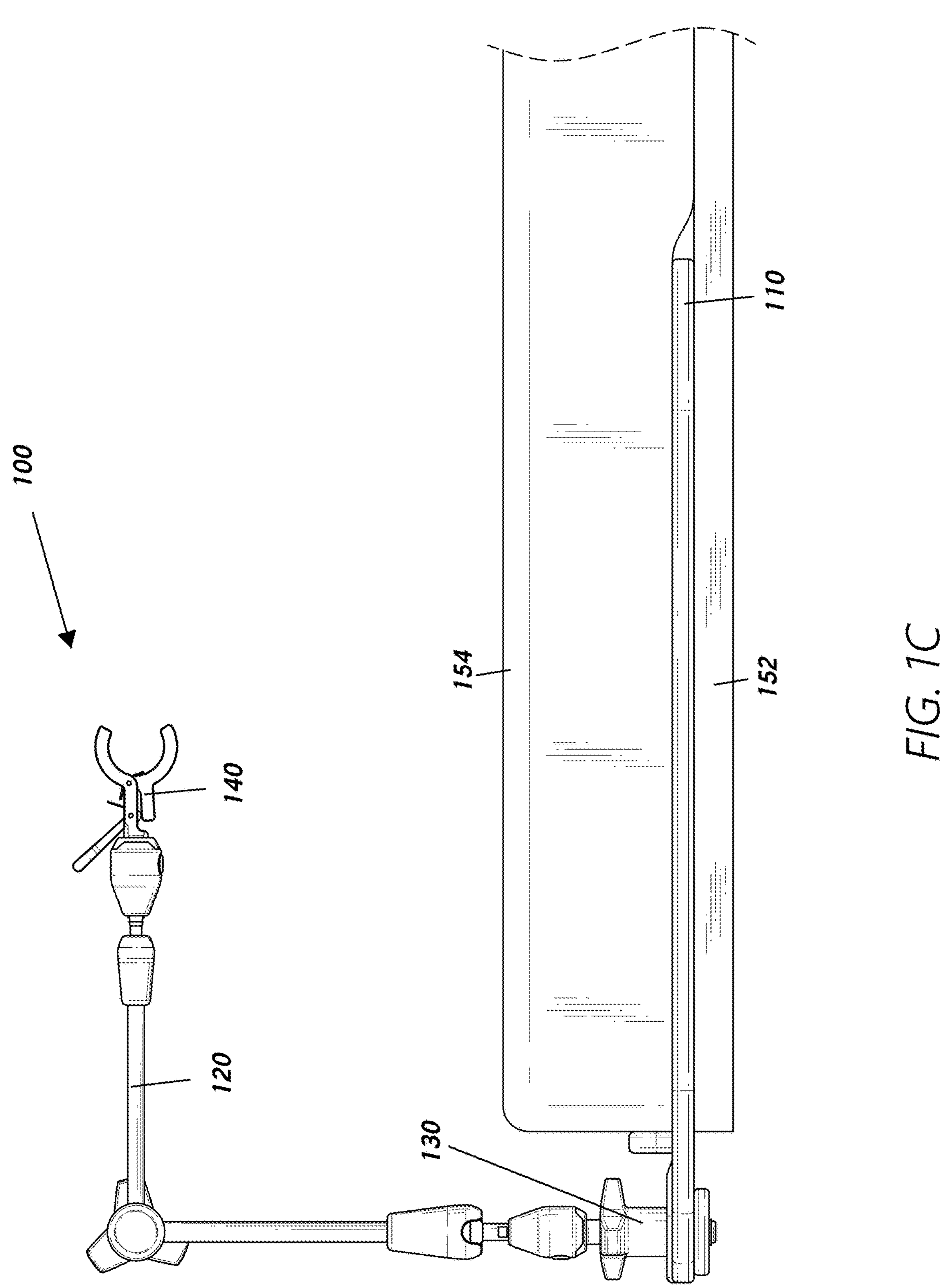

FIGS. 1A, 1B, and 1C illustrate examples of a stabilizer system 100 for use in medical procedures to secure an access sheath or delivery device. FIG. 1A illustrates the example stabilizer system 100 having a base 110, an articulating arm 120, a connector 130, and a holder 140. The base 110 provides a stable platform for the articulating arm 120. The articulating arm 120 is secured to the base 110 via the connector 130. The articulating arm 120 includes the holder 140 at a distal end of the articulating arm 120 to enable stabilization of an access sheath or delivery device 150. The articulating arm 120 and holder 140 are configured to provide freedom of movement to enable desired positioning of the delivery device 150. Further description of the base 110 is provided herein with respect to FIGS. 3A-3D. Further description of the connector 130 is provided herein with respect to FIGS. 4A-4E. Further description of the articulating arm 120 is provided herein with respect to FIGS. 5A and 5B. Further description of the holder 140 is provided herein with respect to FIGS. 6A and 6B.

FIG. 1B illustrates the example stabilizer system 100 with the base 110 positioned between a patient table 152 and a mattress 154. A sterile surgical drape 156 is positioned over the mattress 154 to provide a sterile barrier. The connector 130 connects the articulating arm 120 and holder 140 above the sterile surgical drape 156, in a sterile region, while the base 110 is in a non-sterile region under the sterile surgical drape 156. The connector 130 is configured to press or crush the sterile surgical drape 156 between the connector 130 and the base 110. In this way, the connector 130 is configured to securely couple the articulating arm 120 to the base 110 to provide a stable mechanism for stabilizing a medical device in the holder 140.

FIG. 1C illustrates a side view of the patient table 152 and mattress 154 without the sterile surgical drape to show how the base 110 is positioned between the patient table 152 and the mattress 154. The majority of the base 110 is positioned under the mattress to provide a stable platform for the articulating arm 120. A relatively small portion of the base 110 protrudes from under the mattress 154 to provide a connection platform for the connector 130. This provides a sturdy and predictable surface for attaching the articulating arm 120. The relatively small portion of the base 110 that protrudes from the patient table 152 contributes to the lack of footprint of the stabilizer system 100 relative to other stabilizer systems. In addition, the base 110 can be positioned at a variety of locations between the mattress 154 and the patient table 152 to enable positioning of a medical device in a desired location relative to a patient or to a target anatomy of the patient and to adjust this position from patient to patient, responsive to differences in patient anatomy. For jugular access procedures, the base 110 can be positioned below the patient's neck/chest area.

Figure 2A:
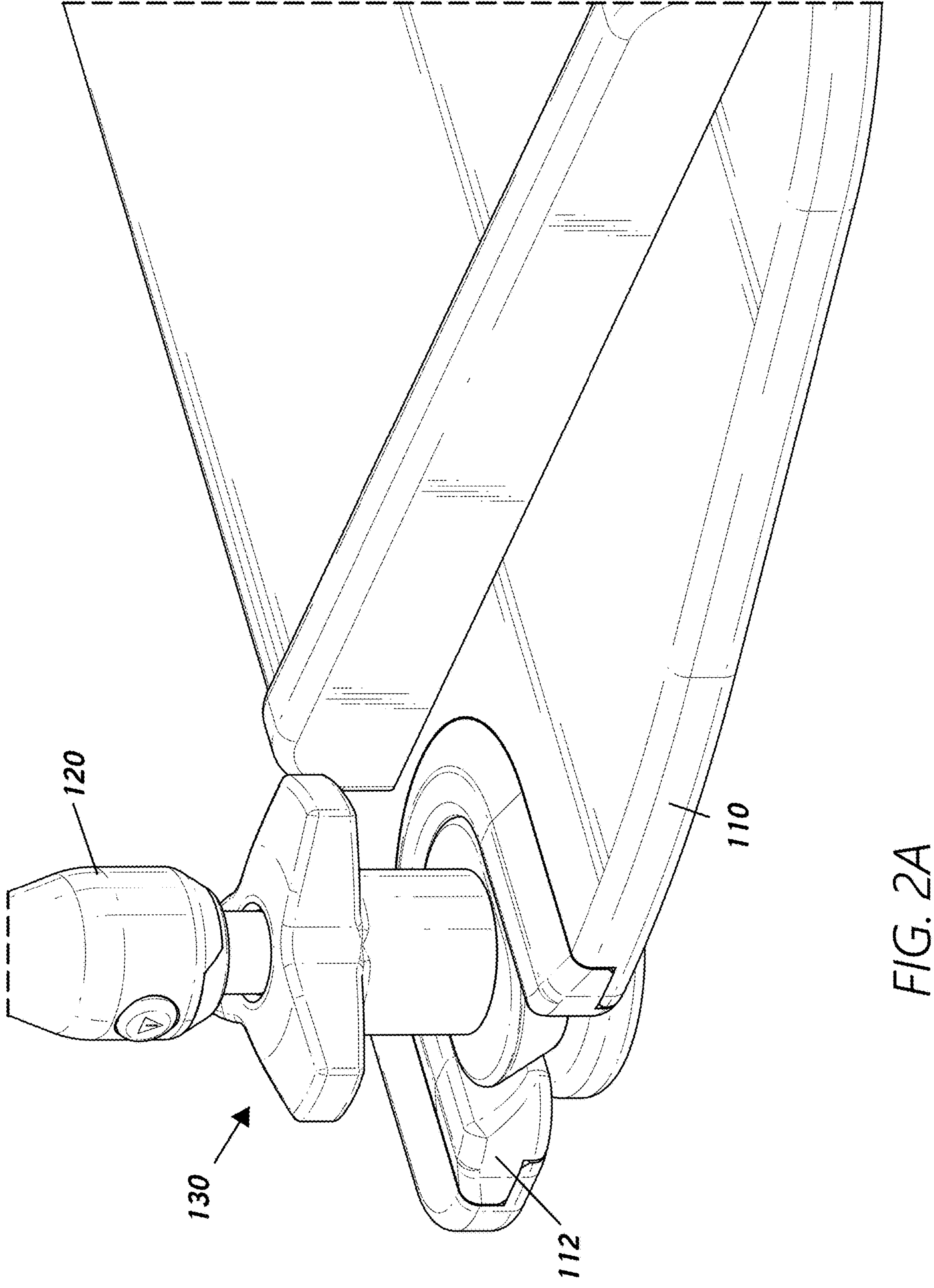
FIGS. 2A, 2B, 2C, and 2D illustrate an example of connecting the connector to the base of the stabilizer system of FIGS. 1A-1C.
Figure 2B:
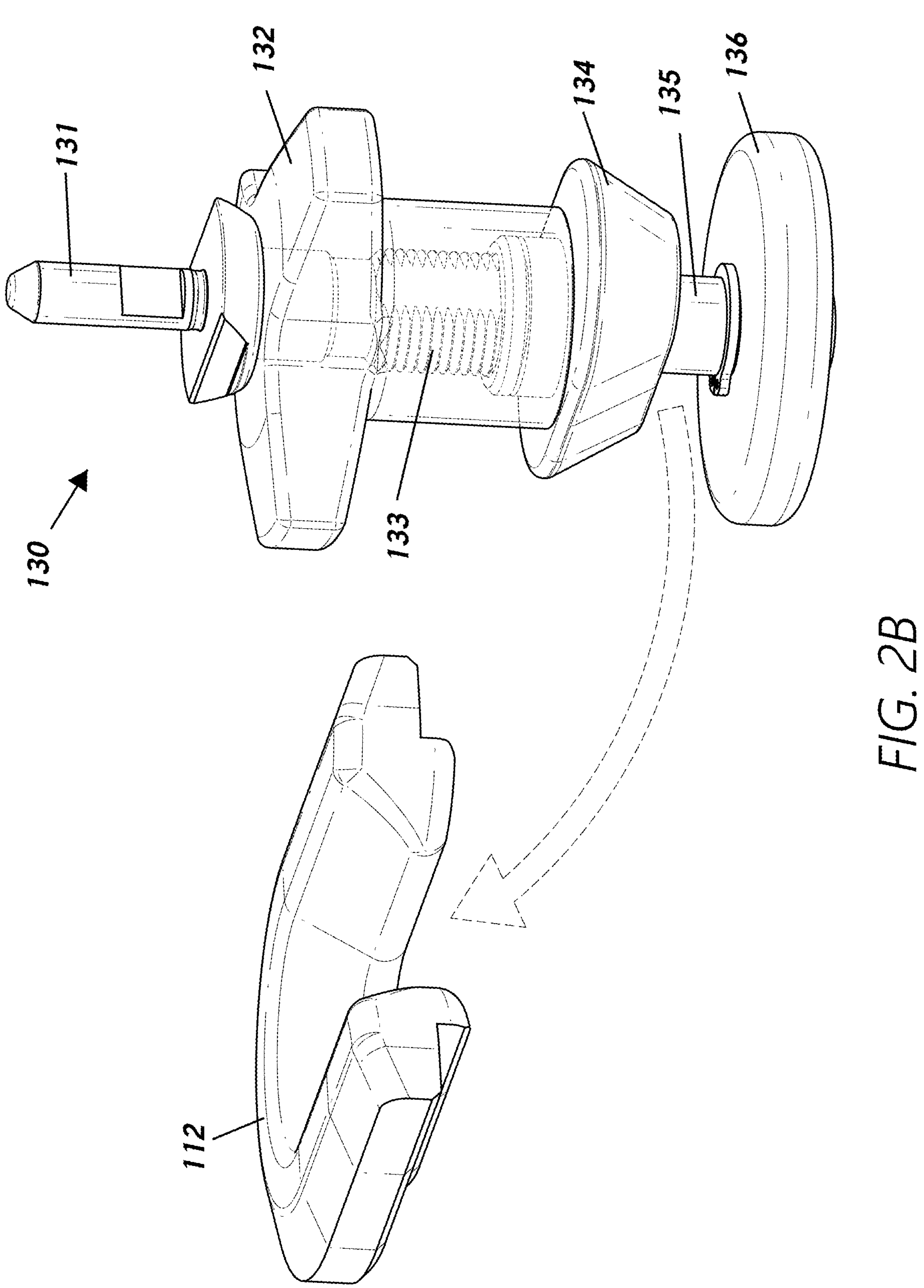
Figure 2D:
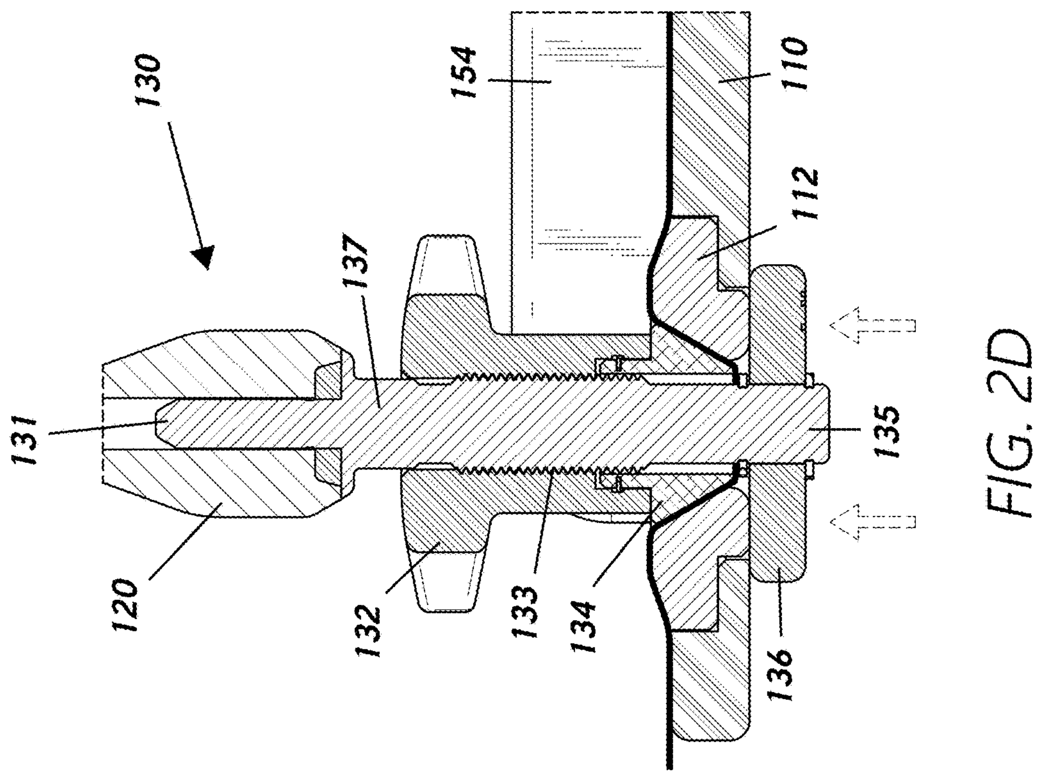
Figure 2C:
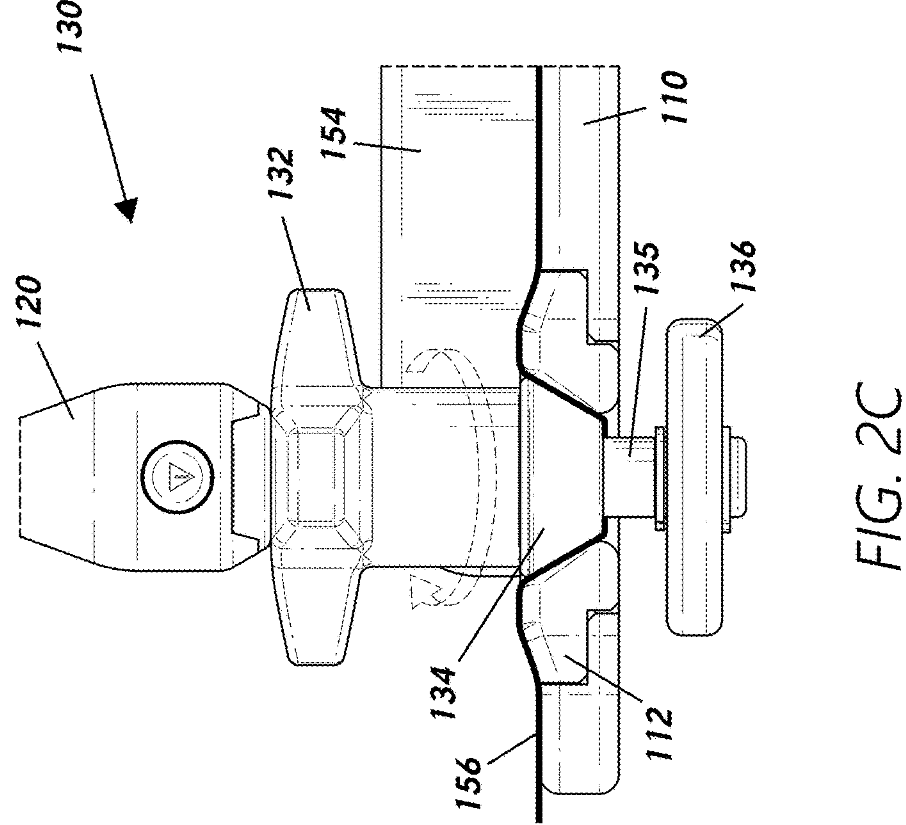

FIGS. 2A, 2B, 2C, and 2D illustrate an example of connecting the connector 130 to the base 110 of the stabilizer system 100 of FIGS. 1A-1C. This example is shown without the sterile drape in FIGS. 2A and 2B for the sake of clarity, but it is to be understood that the connector 130 is configured to be connected to the base 110 with a sterile surgical drape between the connector 130 and base 110 (as shown in FIGS. 2C and 2D).

FIG. 2A illustrates the connector 130 secured to the base 110. In particular, the connector 130 is positioned within a base mounting portion 112 (or a connector interface) of the base 110. The base mounting portion 112 is configured to mate with complementary components of the connector 130, as described in greater detail herein. The articulating arm 120 is mounted to the connector 130 using a mating portion, such as an arm mating pin, as described in greater detail herein. In some embodiments, the base mounting portion 112 can be integrated with the base 110 or it can be separable or otherwise separately made and joined or attached to the base 110.

FIG. 2B illustrates the connector 130 separate from the base mounting portion 112. The connector 130 is in a mounting configuration that enables the connector 130 to be mated with the base mounting portion 112. The connector 130 includes an arm mating pin 131 configured to mate with a corresponding feature on the articulating arm 120 (not shown in FIG. 2B). The arm mating pin 131 enables attachment and removal of the articulating arm 120 from the connector 130. This advantageously allows the connector 130 to be connected to the base mounting portion 112 without the articulating arm 120 being coupled to the connector 130 while that connection is made. This may facilitate maintaining sterility of the articulating arm 120 before and during the medical procedure.

The connector 130 includes a knob 132. The knob 132 is internally threaded. The internal threading of the knob 132 mates with a threaded portion 133 of a shaft 137. The connector 130 includes a tapered clamp plate 134 configured to move along the shaft 137. The tapered clamp plate 134 is held captive to the knob 132 using a grooved ring assembly (not shown). Turning the knob 132 causes the knob 132 to translate relative to the shaft 137. The tapered clamp plate 134 has an oblong, stadium, or pill-shaped, cross-section when viewed from the top (e.g., a horizontal cross-section) and a tapered cross-section when viewed from the side (e.g., a vertical cross-section). The shape of the tapered clamp plate 134 mates with or complements the shape of the base mounting portion 112. The tapered clamp plate 134 is configured to seat within an opening formed by the base mounting portion 112 in such a way that allows a surgical drape to be held between the tapered clamp plate 134 and the base mounting portion 112. The taper of these components facilitates clamping or pressing a surgical drape between the components, accommodating different thicknesses or configurations of surgical drape.

The connector 130 also includes a bottom clamp plate 136 coupled to the shaft 137. The bottom clamp plate 136 is constrained axially relative to the shaft 137 and is configured to freely rotate around the bottom portion 135 of the shaft 137. Turning the knob 132 causes the tapered clamp plate 134 and the bottom clamp plate 136 to approach one another. If seated in the base mounting portion 112, approximation of the tapered clamp plate 134 and the bottom clamp plate 136 causes a clamping force that secures the connector 130 to the base mounting portion 112.

FIGS. 2C and 2D illustrate the procedure for tightening the connector 130 to the base 110 with a surgical drape 156 over the base 110. The connector 130 is seated within the base mounting portion 112 with the surgical drape 156 between the base mounting portion 112 and the connector 130. The base 110 is positioned under a mattress 154, as described elsewhere herein. The articulating arm 120 is attached to the arm mating pin 131 of the connector 130.

FIG. 2C shows that the bottom clamp plate 136 is loose to enable mating of the connector 130 with the base mounting portion 112. The surgical drape 156 is positioned over the base 110. Seating the connector 130 within the base mounting portion 112 causes the surgical drape 156 to be sandwiched between the connector 130 and the base 110. Turning the knob 132 as indicated by the dashed arrow in the figure causes the connector 130 to tighten to clamp the surgical drape 156 between the tapered clamp plate 134 and the base mounting portion 112 and to secure the connector 130 to the base mounting portion 112.

FIG. 2D illustrates the connector 130 in a secured configuration (with a cross-section view to better illustrate the various components). In the secured configuration, the bottom clamp plate 136 abuts a bottom side of the base mounting portion 112 and the tapered clamp plate 134 abuts an upper tapered part of the base mounting portion 112. In this secured configuration, the surgical drape 156 is pressed between the base mounting portion 112 and the tapered clamp plate 134. In some instances, the surgical drape 156 may be pressed between the bottom clamp plate 136 and the bottom of the base mounting portion 112. Turning the knob 132 causes the bottom clamp plate 136 to move upward toward the tapered clamp plate 134 (as indicated by the arrows) by causing the shaft 137 to move upward relative to the knob 132. As illustrated here, the shaft 137 includes the threaded portion 133 of the shaft 137 and the bottom portion 135 of the shaft 137. The bottom portion 135 of the shaft 137 constrains axial movement of the bottom clamp plate 136. The arm mating pin 131 can be formed as part of the shaft 137 or it can be an extension attached to the shaft 137. Movement (axial and rotational) of the arm mating pin 131 is also constrained by the shaft 137. In this figure, the grooved ring assembly can be seen that secures the tapered clamp plate 134 to the knob 132 (a grooved ring assembly 138 being described in greater detail herein with respect to FIGS. 4A-4E).

A horizontal cross-section of the tapered clamp plate 134 is shaped to be complementary to a horizontal cross-section of the opening of the base mounting portion 112. For example, the horizontal cross-section of the tapered clamp plate 134 can be oblong, such as a stadium or pill shape, and the opening formed by the base mounting portion 112 can be similarly oblong with an enclosed end and an open end, such as a horseshoe shape. For example, the horizontal cross-section of the tapered clamp plate 134 can include a rounded end that mates with a rounded portion of the opening formed by the base mounting portion 112 and the horizontal cross-section of the tapered clamp plate 134 can include straight portions extending from the rounded end that mate with straight edges of the opening formed by the base mounting portion 112. The complementary shapes of the tapered clamp plate 134 and the base mounting portion 112 provide stability to the articulating arm 120 to resist rotation caused by forces and/or torques on the articulating arm 120. In some implementations, the horizontal cross-section of the tapered clamp plate 134 can be any suitable regular or irregular shape that deviates from a circular cross-section, such as an ellipse, oval, rectangle, rounded rectangle, square, pill shape, oblong shape, etc. Deviation from a circular cross-section for the tapered clamp plate 134 is advantageous because the tapered clamp plate 134 resists turning or twisting relative to the base mounting portion 112 when forces and/or torques are applied to the articulating arm 120. The advantages of the complementary oblong shapes of the tapered clamp plate 134 and the base mounting portion 112 can be realized in other configurations of a connector and a base mounting portion and need not be limited to embodiments of connectors and base mounting portions configured as described in FIGS. 2A-4E.

A typical process for preparing the stabilizer systems disclosed herein to maintain sterility involves placing the base 110 between the mattress 154 and the patient table 152 (under the patient) prior to preparing the other components. Once the patient and base 110 are in place, a sterile surgical drape 156 is positioned over the patient and the base 110. On a separate, sterile prep table, the articulating arm 120, connector 130, and holder 140 are assembled. These sterile components are then connected to the base 110 over the surgical drape 156 to maintain sterility of the assembled components. Thus, the base 110 is in a non-sterile region while the connector 130, articulating arm 120, and holder 140 are in a sterile region and that sterile barrier defined by the surgical drape 156 is maintained prior to and after connecting the assembled articulating arm 120 to the base 110.

Figure 3A:
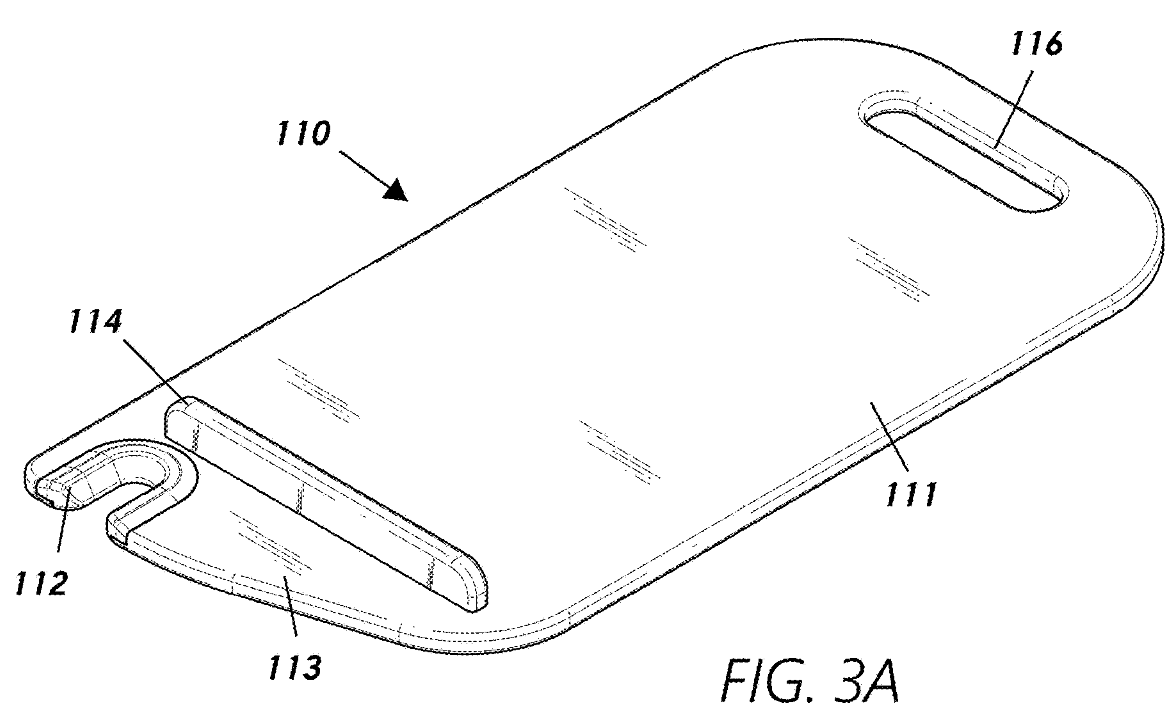
FIGS. 3A, 3B, 3C, and 3D illustrate the base of the stabilizer system of FIGS. 1A-1C.
Figure 3B:
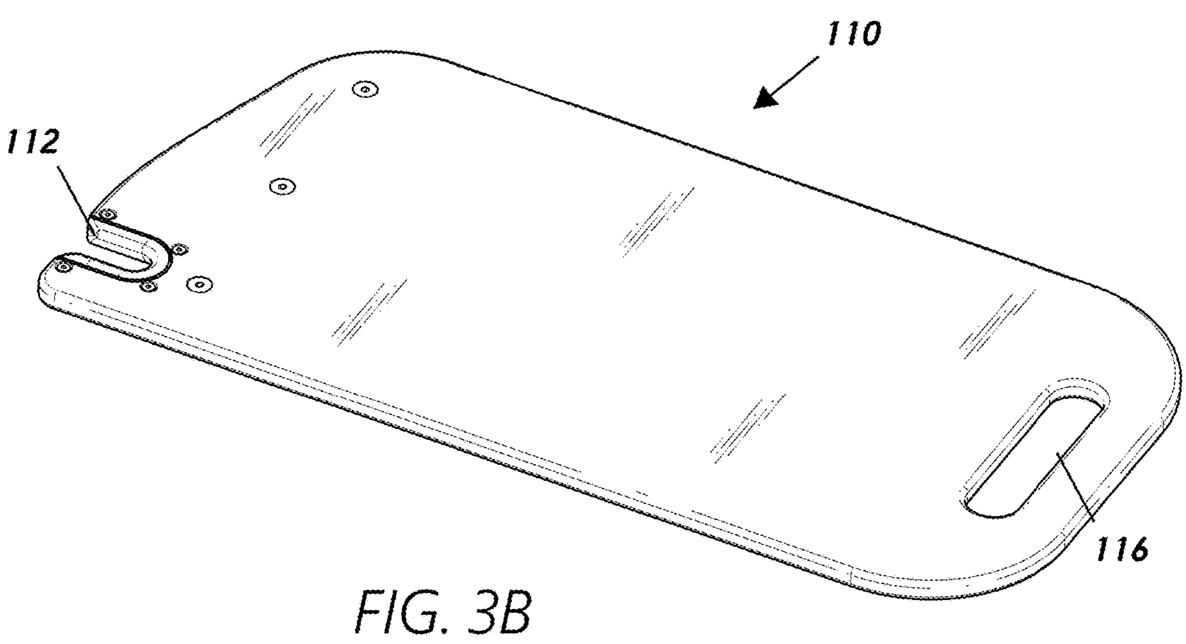
Figure 3C:
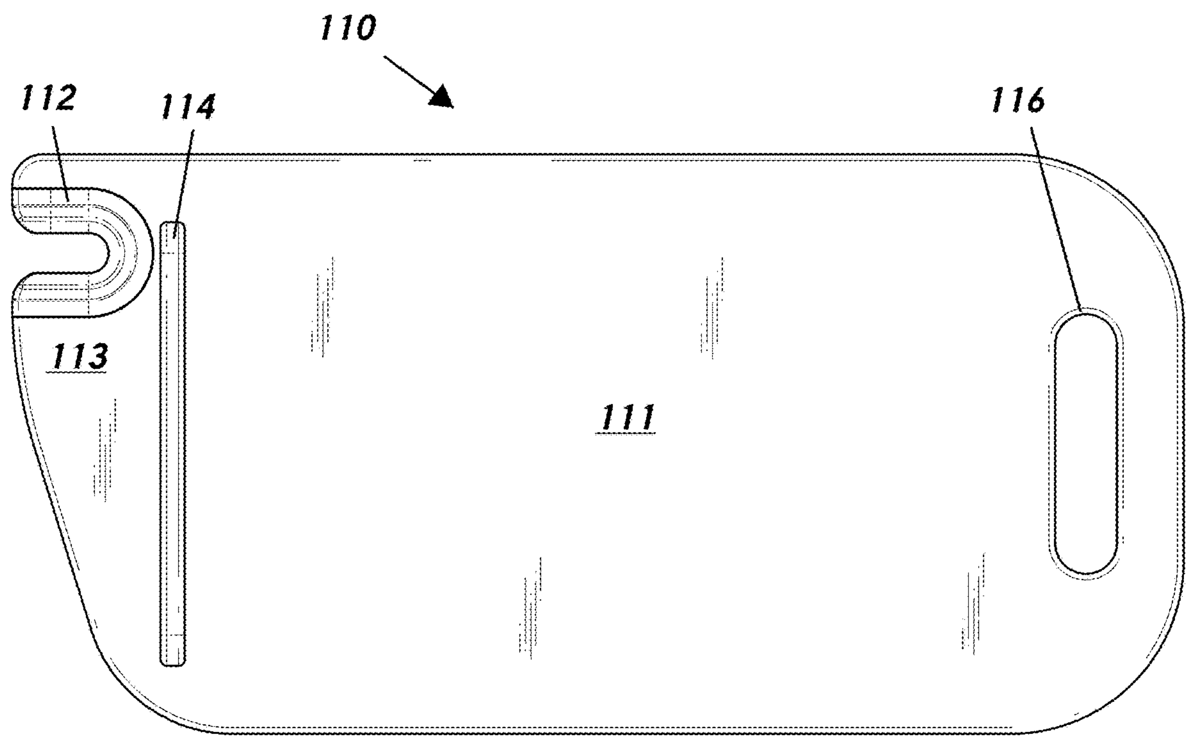
Figure 3D:
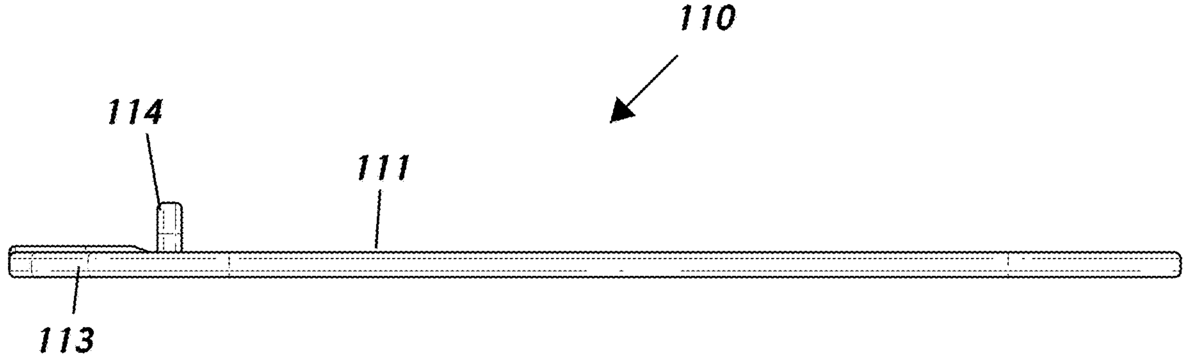

FIGS. 3A, 3B, 3C, and 3D illustrate the base 110 of the stabilizer system 100 of FIGS. 1A-1C. FIG. 3A illustrates an angled view of the top of the base 110, FIG. 3B illustrates an angled view of the bottom of the base 110, FIG. 3C illustrates a top view of the base 110, and FIG. 3D illustrates a side view of the base 110. The base 110 includes a stabilizing portion 111 and a protruding portion 113. The stabilizing portion 111 is configured to be placed between a mattress or pad and a patient table to secure the base 110 to the patient table. With the stabilizing portion 111 of the base 110 positioned in that manner, the protruding portion 113 extends outward from between the mattress and the patient table to expose the base mounting portion 112. This enables the connector 130 to be secured to the base 110 as described herein with reference to FIGS. 2A-2D.

The base 110 includes a wall 114 that extends vertically from the base 110. The wall 114 is configured to provide a stop for inserting the base 110 between the patient table and mattress and thus separates the stabilizing portion 111 from the protruding portion 113 of the base 110. In some implementations, the base 110 does not include the wall 114. The base 110 can include a handle 116 for ease of handling. In some implementations, the base 110 does not include the handle 116. It is to be understood that although a specific example is provided for the base 110, the base 110 can be any of a variety of platforms that fit between a mattress and table and that support a connector while maintaining sterility of a sterile side of a sterile barrier.

The base 110 can be radiolucent to not interfere with x-ray imaging and/or to be transparent to fluoroscopy. In some embodiments, the base 110 is made of a plastic. In certain embodiments, the base mounting portion 112 includes metal or other hard and strong material to bolster the mounting strength of the base 110.

Figure 4B:
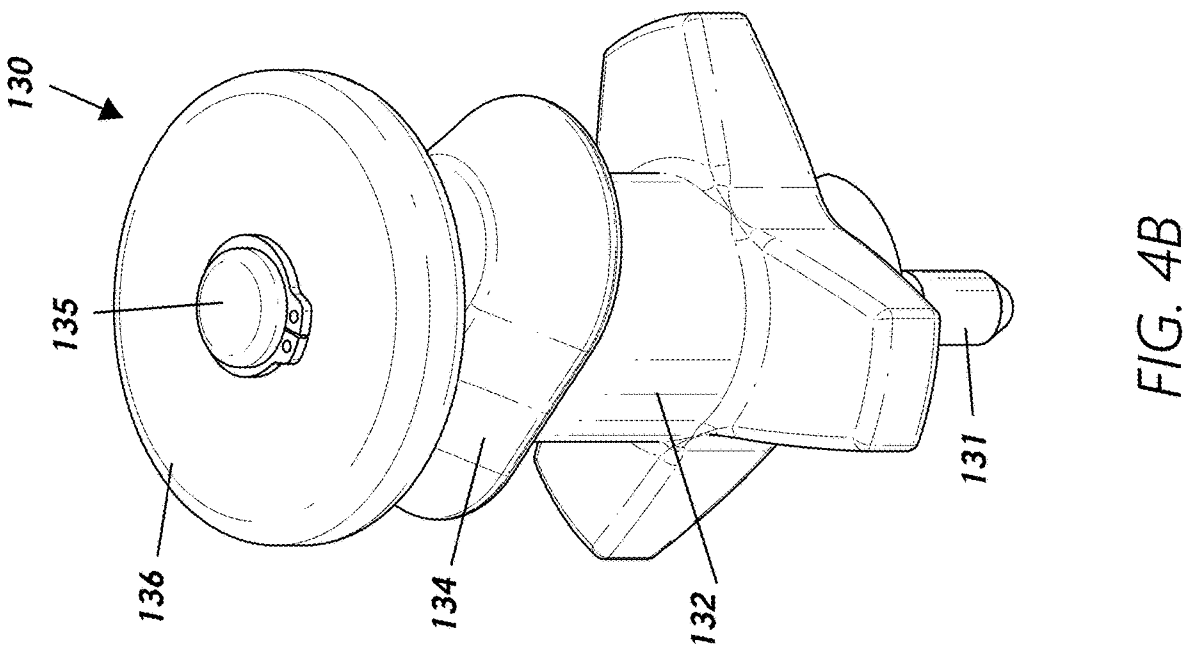
FIGS. 4A, 4B, 4C, 4D, and 4E illustrate the connector of the stabilizer system of FIGS. 1A-1C.
Figure 4A:
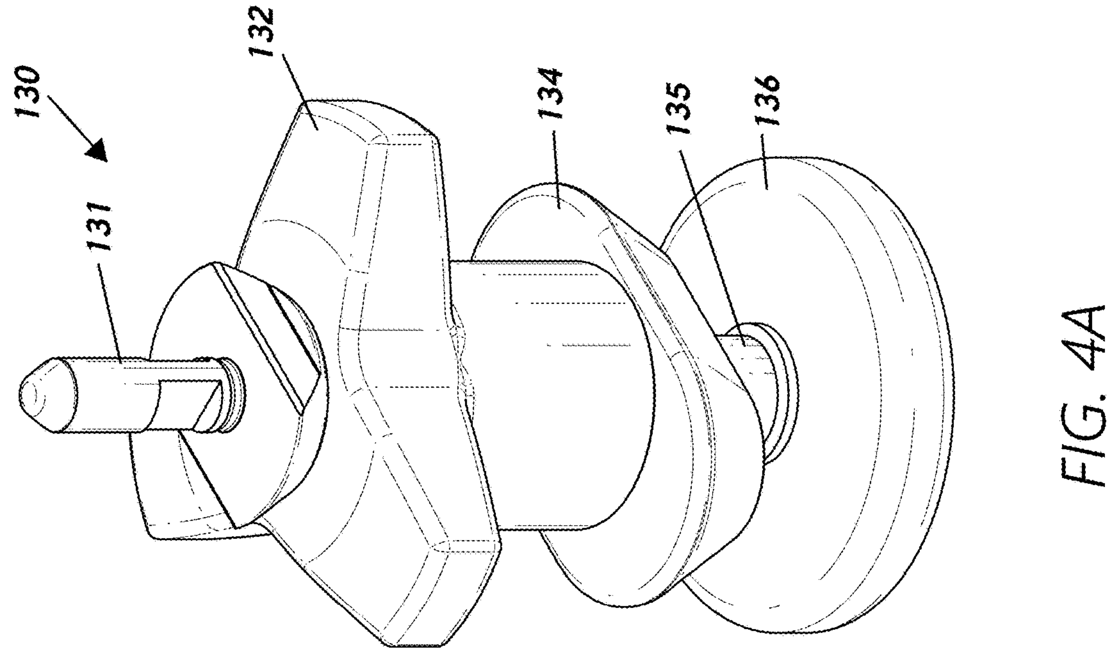
Figure 4D:
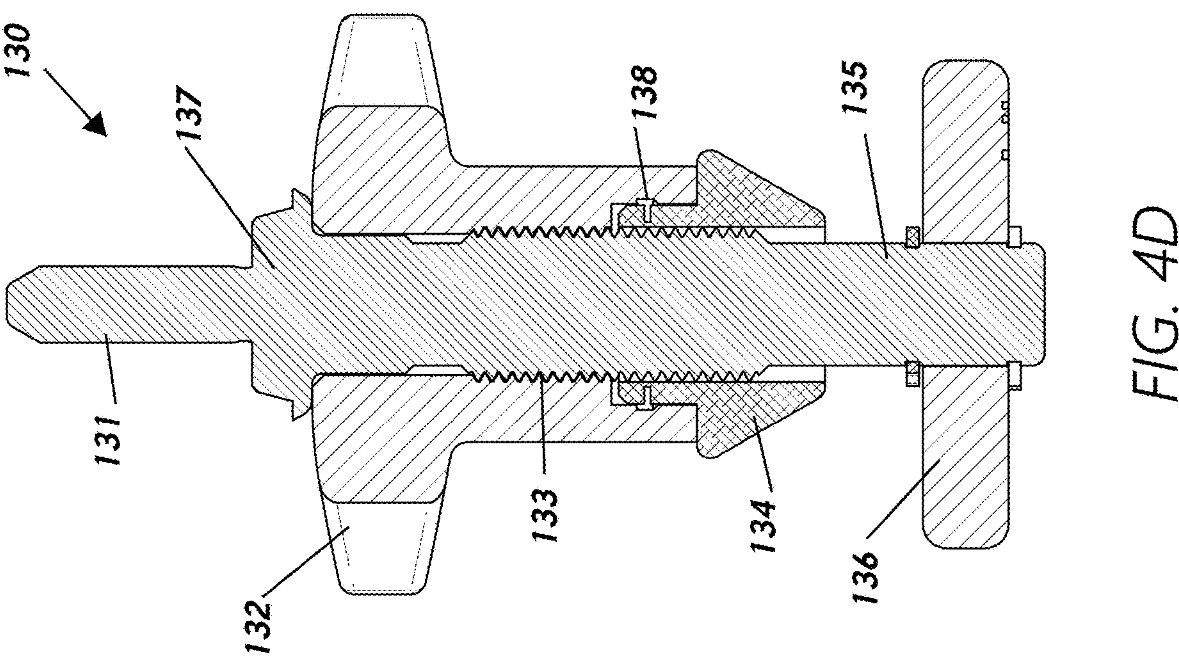
Figure 4C:
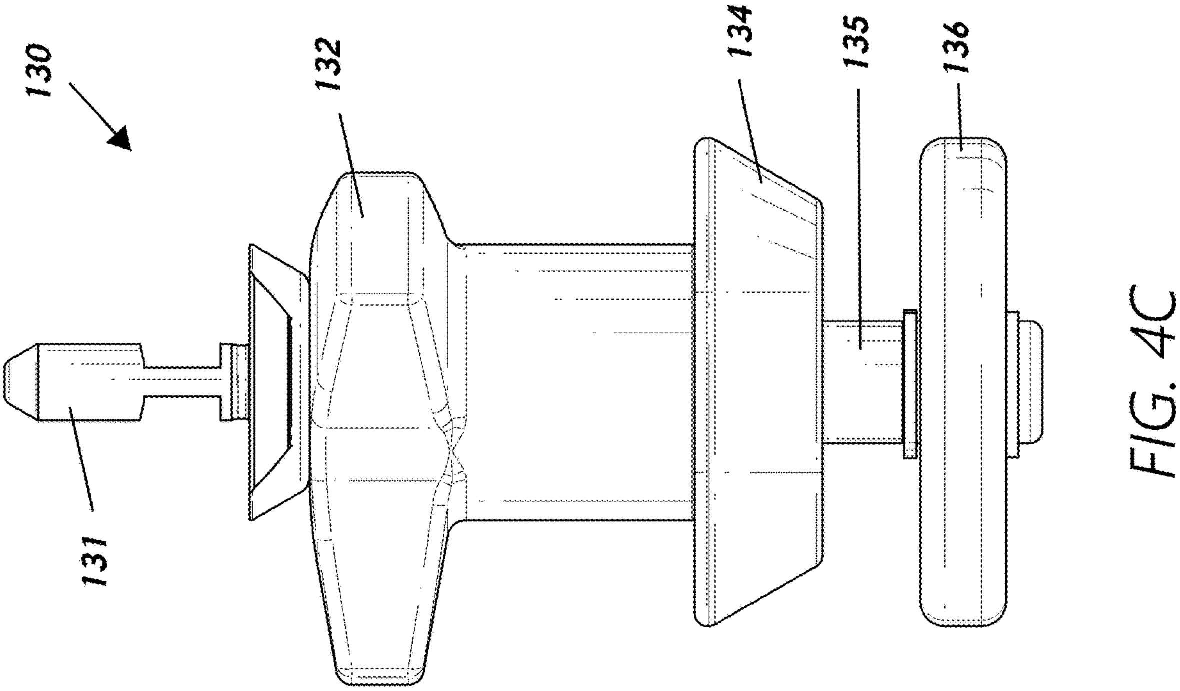
Figure 4E:
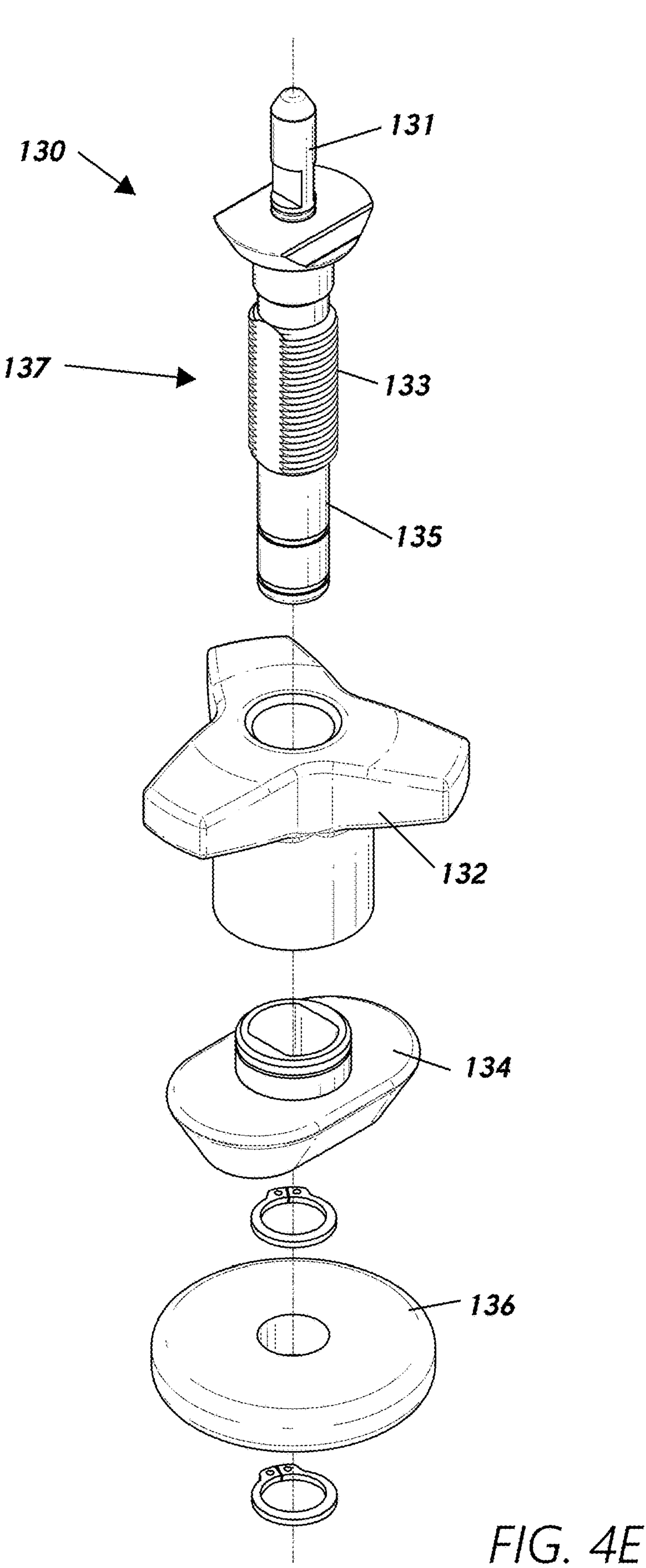

FIGS. 4A, 4B, 4C, 4D, and 4E illustrate the connector 130 of the stabilizer system 100 of FIGS. 1A-1C. FIG. 4A illustrates an angled view of the connector 130 from the top, FIG. 4B illustrates an angled view of the connector 130 from the bottom, FIG. 4C illustrates a side view of the connector 130, FIG. 4D illustrates a cross-section view of the connector 130, and FIG. 4E illustrates an exploded view of the connector 130. As described herein with reference to FIGS. 2A-2D, the connector 130 includes an arm mating pin 131 configured to couple to an articulating arm, such as the articulating arm 120 described herein. The connector 130 includes the knob 132 that is internally threaded. The internal threading of the knob 132 mates with the threaded portion 133 of the shaft 137. Rotating the knob 132 causes the knob 132 to translate axially along the shaft 137 (the shaft 137 comprising the threaded portion 133 of the shaft 137, the bottom portion 135 of the shaft 137, and the arm mating pin 131). The connector 130 includes the tapered clamp plate 134 affixed or secured to the knob 132 by way of a grooved ring assembly 138. Thus, as the knob 132 rotates and translates axially along the shaft 137, the tapered clamp plate 134 translates axially along the shaft 137 as well. The connector 130 includes the bottom clamp plate 136 that moves toward the tapered clamp plate 134 responsive to rotation of the knob 132. The bottom clamp plate 136 is axially fixed relative to the bottom portion 135 of the shaft 137 but is free to rotate around the bottom portion 135 of the shaft 137.

The tapered clamp plate 134 has an oblong or pill shape when viewed from the top and a tapered cross-section when viewed from the side. The pill shape mates with or is complementary to a correspondingly shaped mounting portion for the base to resist torques arising from the articulating arm 120. The complementary tapered shapes enable secure connection between the connector 130 and the base 110 with a surgical drape of an unknown thickness (or a variety of different surgical drapes with different thicknesses) between the connector 130 and the base 110. It is to be understood that although a specific example is provided for the connector 130, the connector can be any of a variety of connectors that interface with a base, examples of which are provided herein.

The tapered clamp plate 134 can be internally keyed to a cross-section of the shaft 137. For example, the tapered clamp plate 134 has an internal opening that is oblong or pill shaped to match an oblong or pill shape of the cross-section of the shaft 137 (seen as part of the threaded portion 133 of the shaft 137 in FIG. 4E. The keying of the internal opening of the tapered clamp plate 134 with the shaft 137 resists or prohibits rotation of the tapered clamp plate 134 relative to the shaft 137. Thus, the combination of the keying of the tapered clamp plate 134 with the shaft 137 and the complementary shapes of the tapered clamp plate 134 and the base mounting portion 112 results in the connector 130 being rigidly connected to the base 110 to resist torques and forces input to the connector 130 via the articulating arm 120. This is advantageous because the articulating arm 120 may be long relative to the size of the connector 130, making it capable of generating substantial torques on the connector 130, and the mechanically robust connection described herein is configured to resist those torques to maintain stability during medical procedures.

Figure 5A:
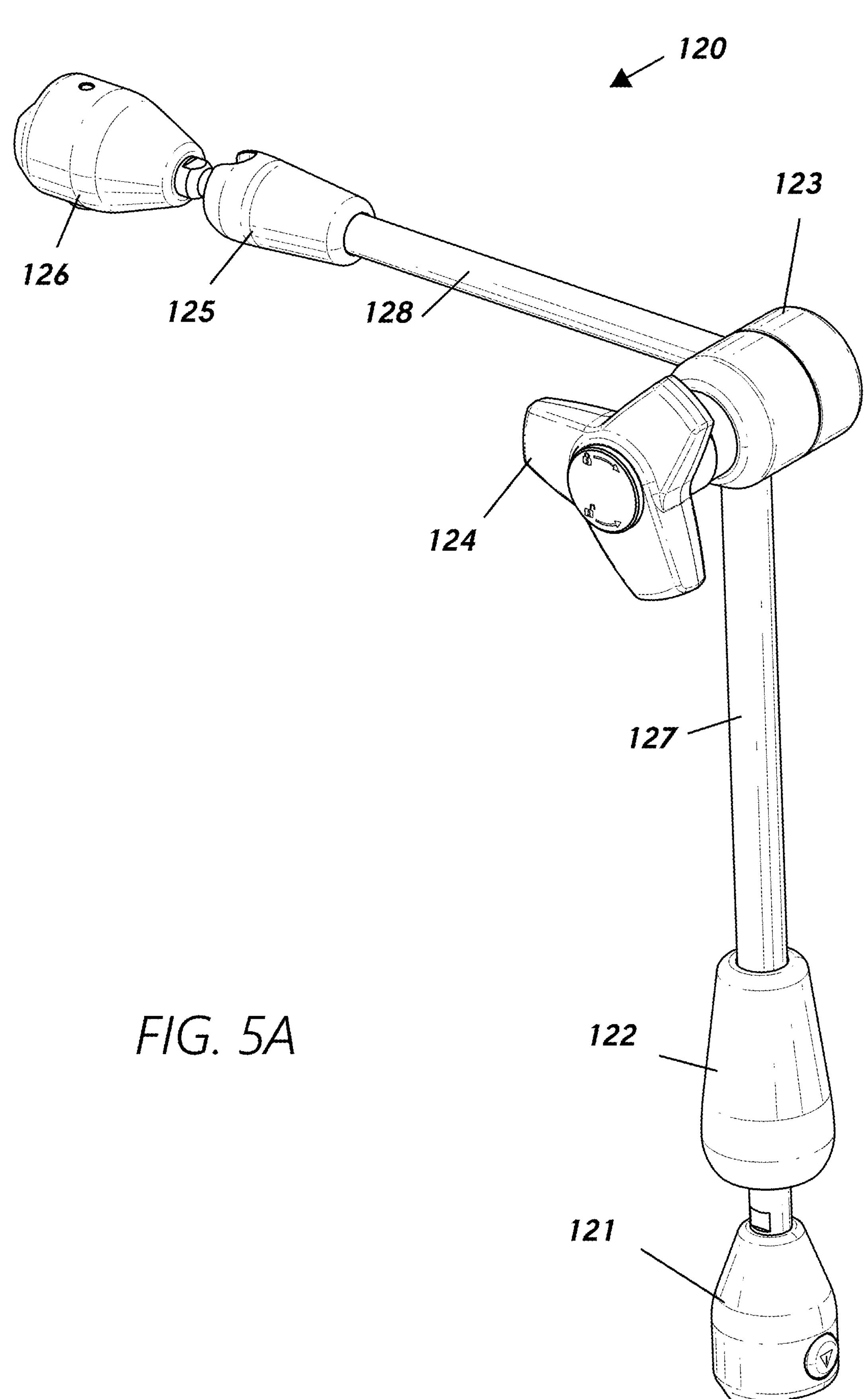
FIGS. 5A and 5B illustrate the articulating arm of the stabilizer system of FIGS. 1A-1C.
Figure 5B:
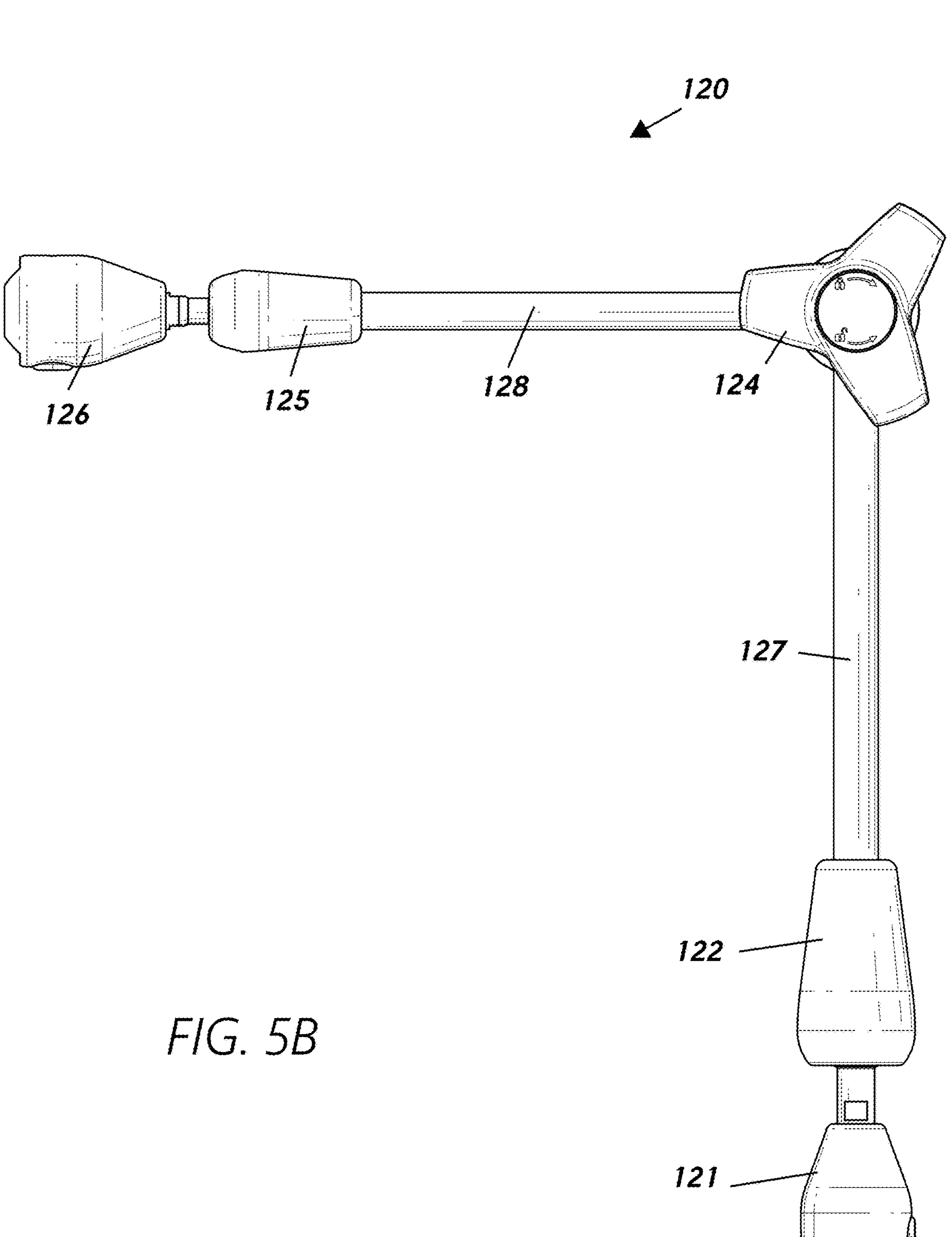

FIGS. 5A and 5B illustrate the articulating arm 120 of the stabilizer system 100 of FIGS. 1A-1C. The articulating arm 120 includes a mating connector 121 configured to mate with the arm mating pin of the connector 130. In some embodiments, the articulating arm 120 includes another type of connection element that interfaces with another type of connector, examples of variations of connectors provided herein. The articulating arm 120 includes a rotational engagement mechanism 122 that can be tightened and loosened to respectively disable and enable rotation of a vertical post 127 with respect to the mating connector 121. The vertical post 127 extends from the mating connector 121 to a rotational hinge 123. The rotational hinge 123 can be loosened to enable rotation or tightened to disable rotation using the hinge lock 124. From the rotational hinge 123 extends an extension arm 128. The angle of the rotational hinge 123 controls an angle or direction of extension of the extension arm 128. The articulating arm 120 includes a holder rotational engagement mechanism 125 that couples a holder interface 126 to the extension arm 128. The holder rotational engagement mechanism 125 controls an orientation of the holder interface 126 (and, thus, a holder mounted to the holder interface 126) and it can be tightened and loosened to control the orientation of the holder interface 126. The articulating arm 120 can be lockable once it is positioned in a desirable configuration. The articulating arm 120 can be releasably attached to the connector 130. It is to be understood that although a specific example is provided for the articulating arm 120, the articulating arm 120 can be any of a variety of movable, positionable articulating arms.

Figure 6A:
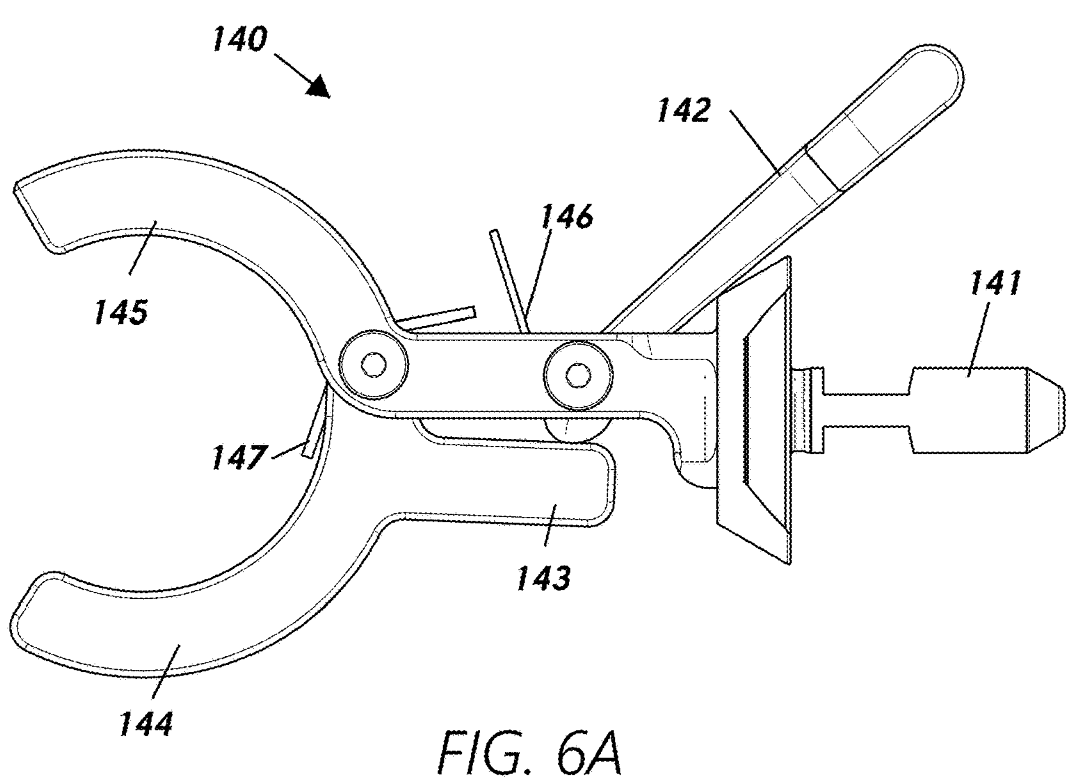
FIGS. 6A and 6B illustrate the holder of the stabilizer system of FIGS. 1A-1C.
Figure 6B:
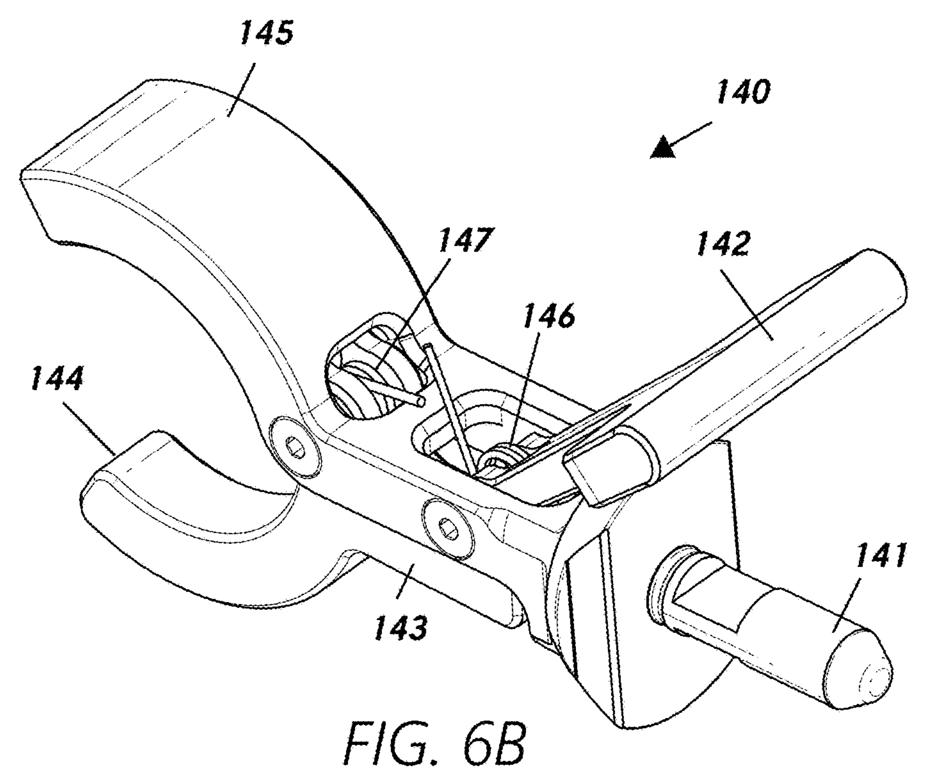

FIGS. 6A and 6B illustrate the holder 140 of the stabilizer system 100 of FIGS. 1A-1C. The holder 140 includes an arm mating pin 141, similar to the arm mating pin 131 of the connector 130, that is configured to mate with the holder interface 126 of the articulating arm 120 to secure the holder 140 to the articulating arm 120. The holder 140 includes a lever 142 that provides provide one-handed operation using a two-stage clamping mechanism. A medical device can be placed in the holder 140 between a first jaw 144 and a second jaw 145. A relatively weak force is applied due to pre-tensioned springs 146, 147 in the holder 140. This force is sufficient to hold the medical device in place. The lever 142 is then actuated by rotating it away from the arm mating pin 141 to increase the force on the medical device by interacting with the jaw extension 143 of the first jaw 144 to rotate the first jaw 144 toward the second jaw 145. This can be accomplished with one hand in most instances. The holder 140 can be configured to be releasably attached to the articulating arm 120. It is to be understood that although a specific example is provided for the holder 140, the holder 140 can be any of a variety of clamping or securing mechanisms for interfacing with or holding an access sheath or delivery system during a procedure (e.g., a jugular procedure).

Additional Example Connectors

As disclosed herein, connectors can be used to connect an articulating arm to a base while maintaining a sterile barrier. The connector connects to the base with a sterile drape coupled between them in a way that allows the connector to connect to the base while the base is covered by the sterile drape. The connectors are configured to securely the join the articulating arm to the base while also maintaining sterility of the articulating arm. The following description and figures illustrate examples of connectors or connector assemblies for a stabilizer system, such as the stabilizer system 100.

A connector assembly can be used to refer to the connector and the connector interface of the base (e.g., the base mounting portion) that interfaces with the connector. The connector assembly includes two main components to attach the base to a mating accessory device, such as the articulating arm, over the sterile drape. The first component of the connector assembly is configured to be attached to or integrated with the base. The first component is non-sterile. The first component is configured to receive or fit into a second component of the connector. The second component of the connector is attached to or integrated with the accessory device (e.g., the articulating arm) to be attached to the base. The second component of the connector assembly is sterile during the procedure and maintains sterility while being attached to the first component of the connector assembly. The connector can be configured in a variety of ways, some of which will be described with respect to the following figures.

Figure 7A:
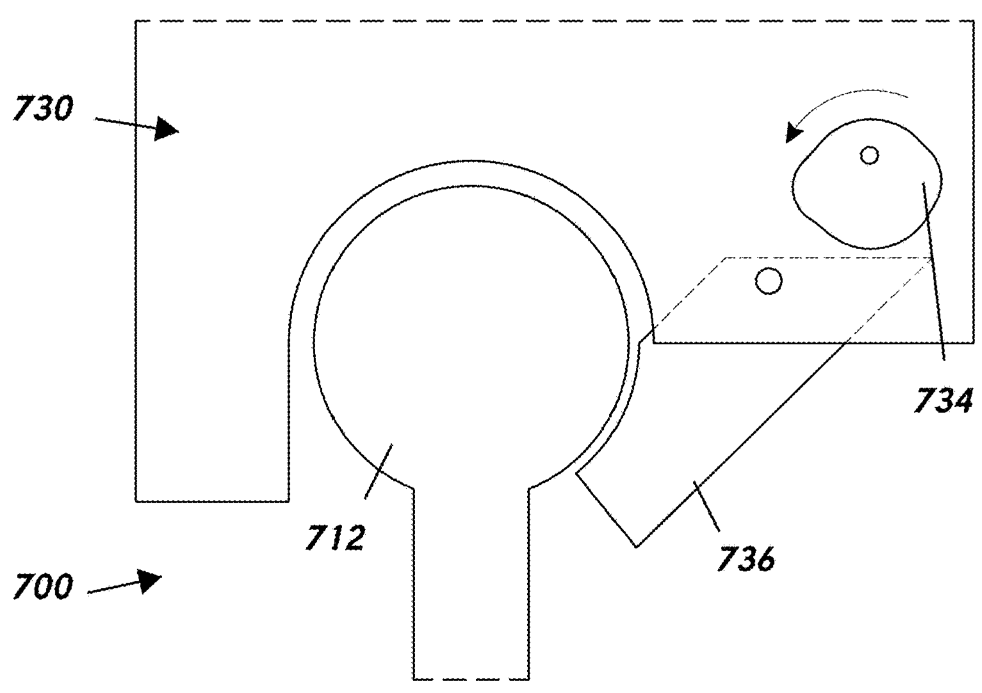
FIGS. 7A and 7B illustrate another example connector assembly.
Figure 7B:
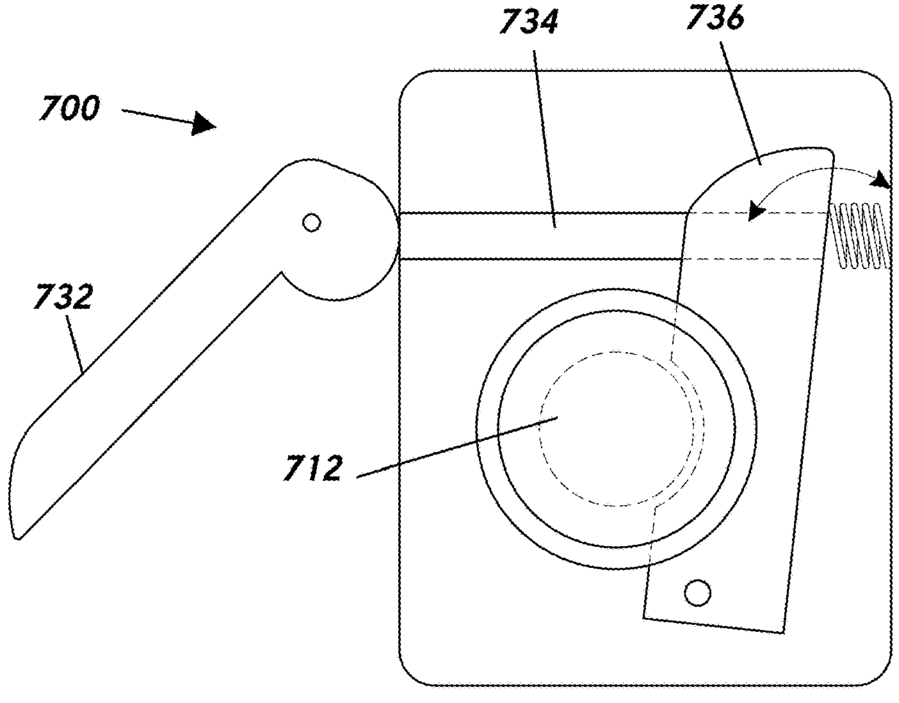

FIGS. 7A and 7B illustrate another example connector assembly 700. FIG. 7A illustrates a side view of the connector assembly 700 and FIG. 7B illustrates a top view of the connector assembly 700. The connector assembly 700 includes a connector 730 comprising a cam driven/locking ball and a base mounting interface comprising a hitch 712, similar to a "tow hitch" connection for a vehicle. The lever 732 can be either side-mounted or top-mounted. The hitch 712 can stick up from the base. The hitch 712 enables a variety of mounting orientations for the connector 730. The lever 732 actuates a cam 734 that moves a latch 736 under the hitch 712 to secure the hitch 712 within the housing of the connector 730. The latch 736 is configured to apply an upward force on the bottom of the hitch 712 to in effect pull the hitch 712 into the housing of the connector 730 to secure the connector 730 to the hitch 712.

Figure 8A:
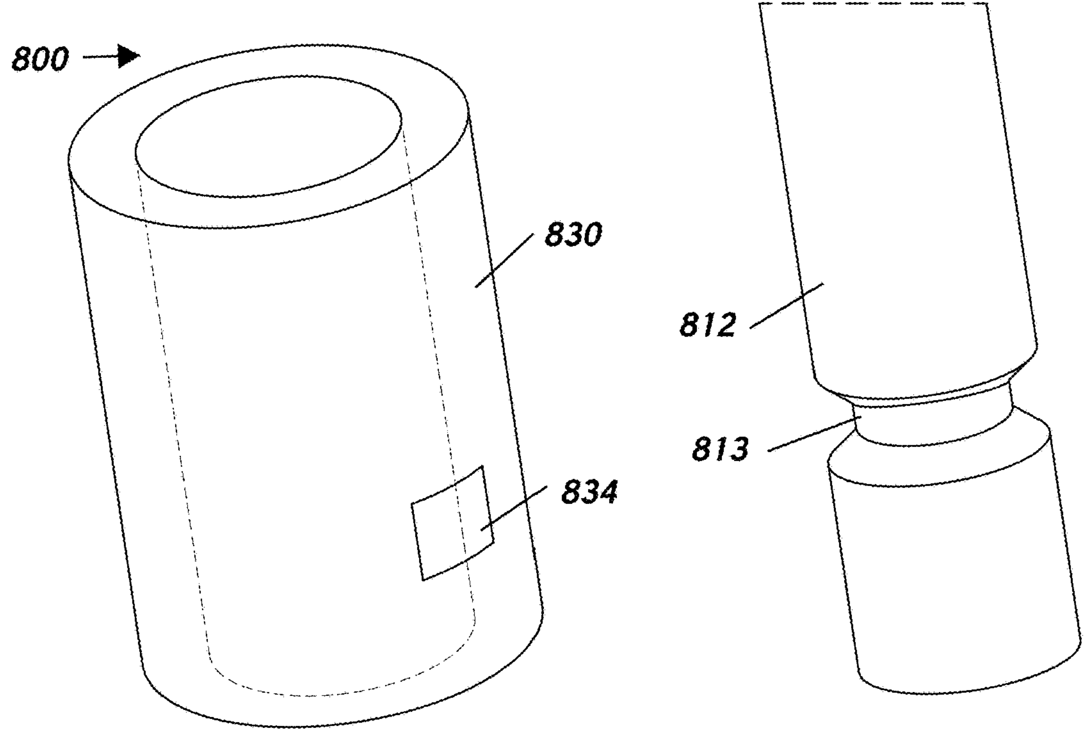
FIGS. 8A and 8B illustrate another example connector assembly that includes a connector interface comprising a dual-tapered pin and a connector comprising a spring-actuated self-latching and locking cam lever.
Figure 8B:
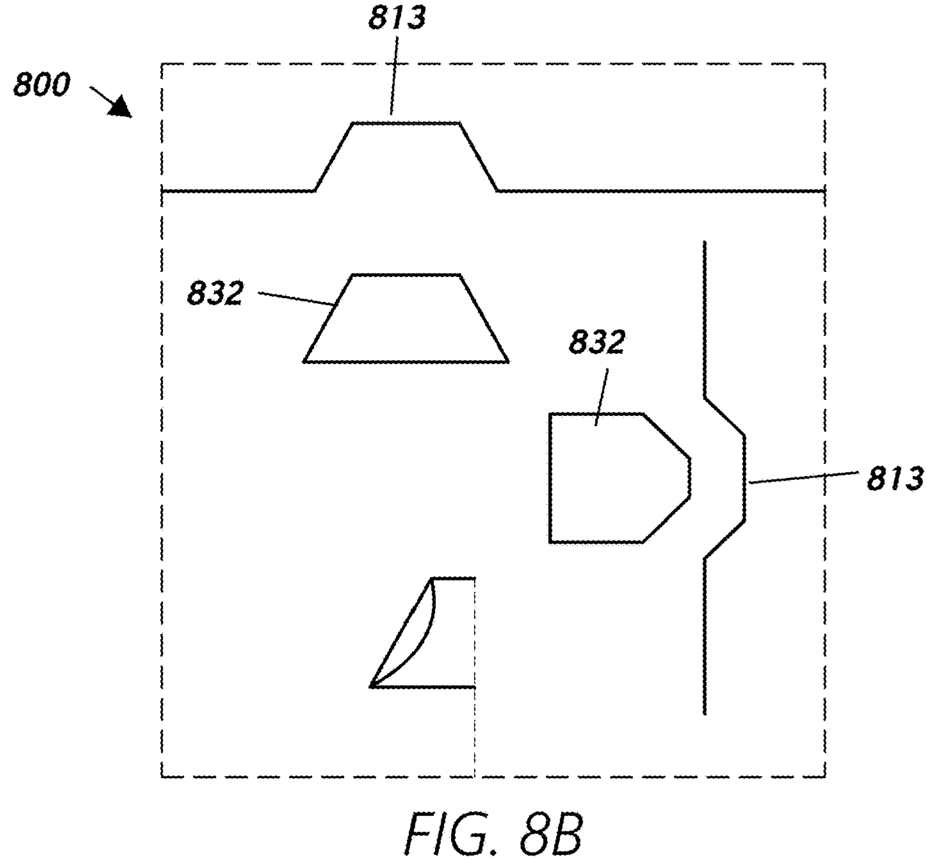

FIGS. 8A and 8B illustrate another example connector assembly 800 that includes a connector interface 812 comprising a dual-tapered pin and a connector 830 comprising a spring-actuated self-latching and locking cam lever. The dual-tapered pin 812 is inserted into the conduit formed by the connector 830. A screw 832 with a head that matches the groove 813 of the dual-tapered pin 812 is inserted through the window 834 to secure the pin 812 within the connector housing.

Figure 9:
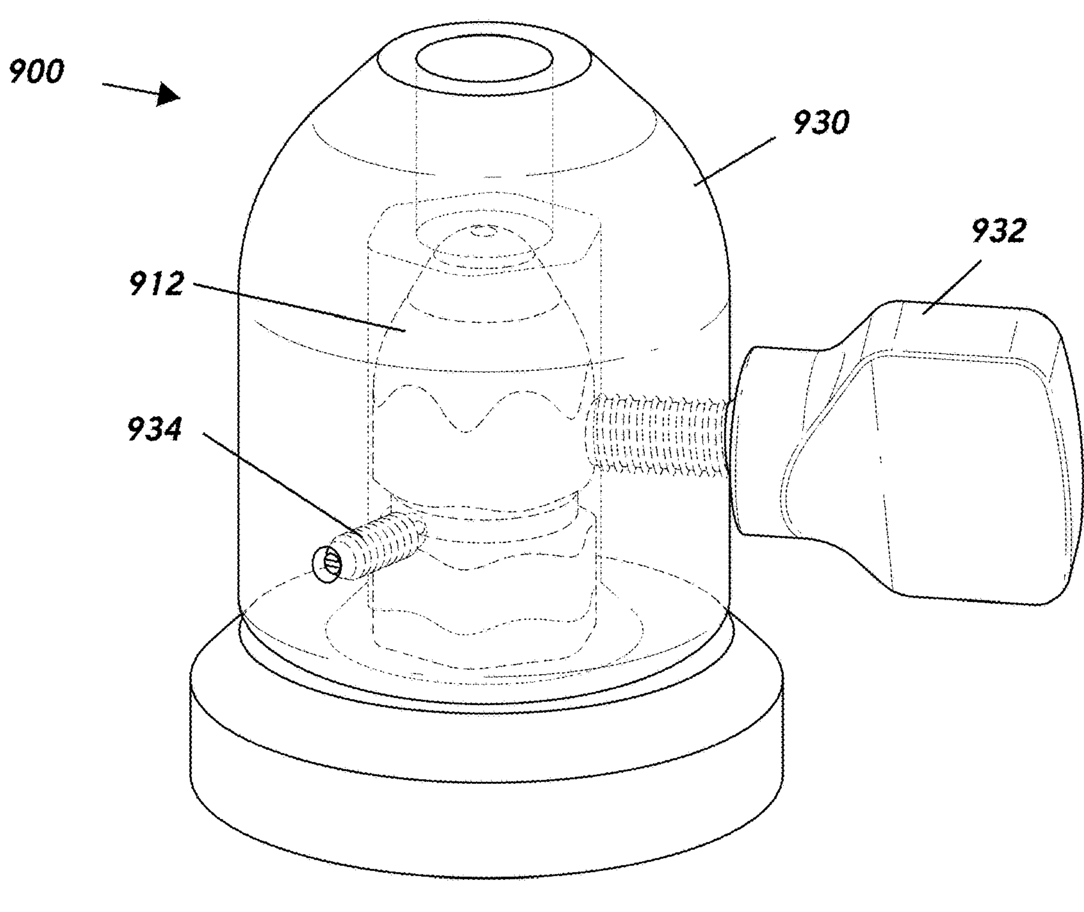
FIG. 9 illustrates another example connector assembly that includes a connector interface comprising a keyed pin and a connector comprising a mating socket with spring plunger latch/seating mechanism and set screw locking mechanism.

FIG. 9 illustrates another example connector assembly 900 that includes a connector interface 912 comprising a keyed (e.g., hexagonal) pin and a connector 930 comprising a mating socket with spring plunger latch/seating mechanism 932 and set screw locking mechanism 934. The set screw 934 can be a simple set screw or it can have a profiled tip or profiled plunger to increase surface area engagement.

Figure 10:
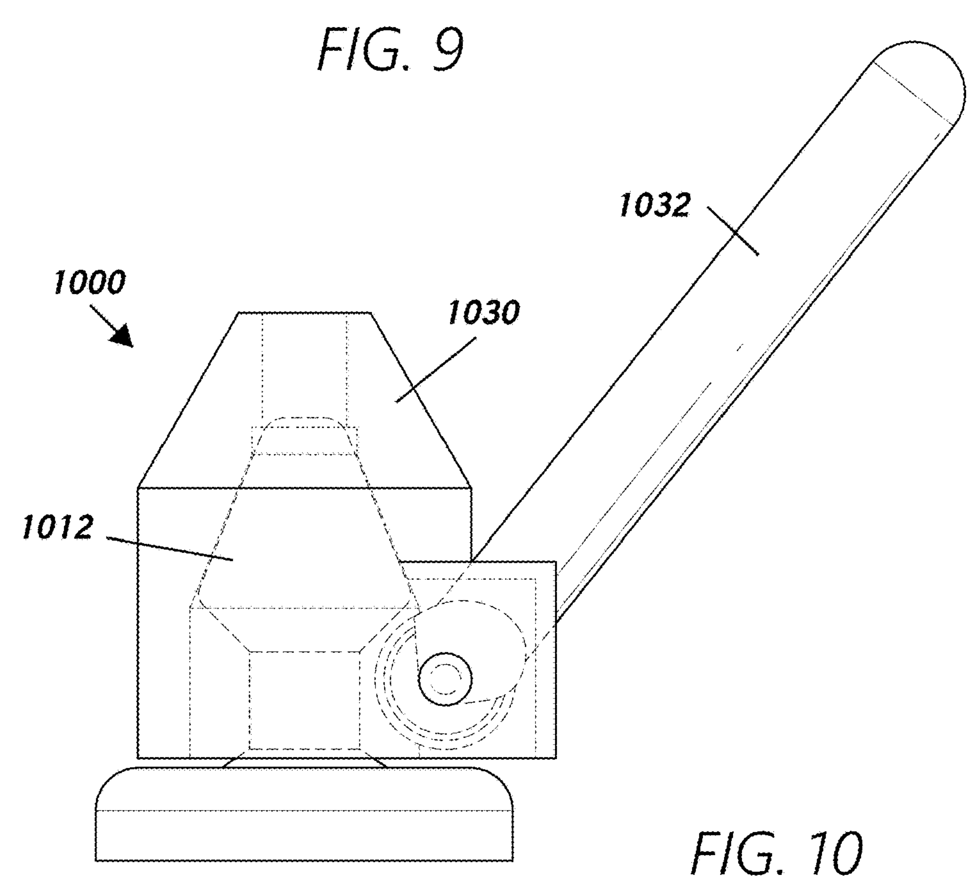
FIG. 10 shows another example connector assembly that includes a connector comprising a lever-actuated collet and a connector interface comprising a mating circular pin.
Figure 11A:
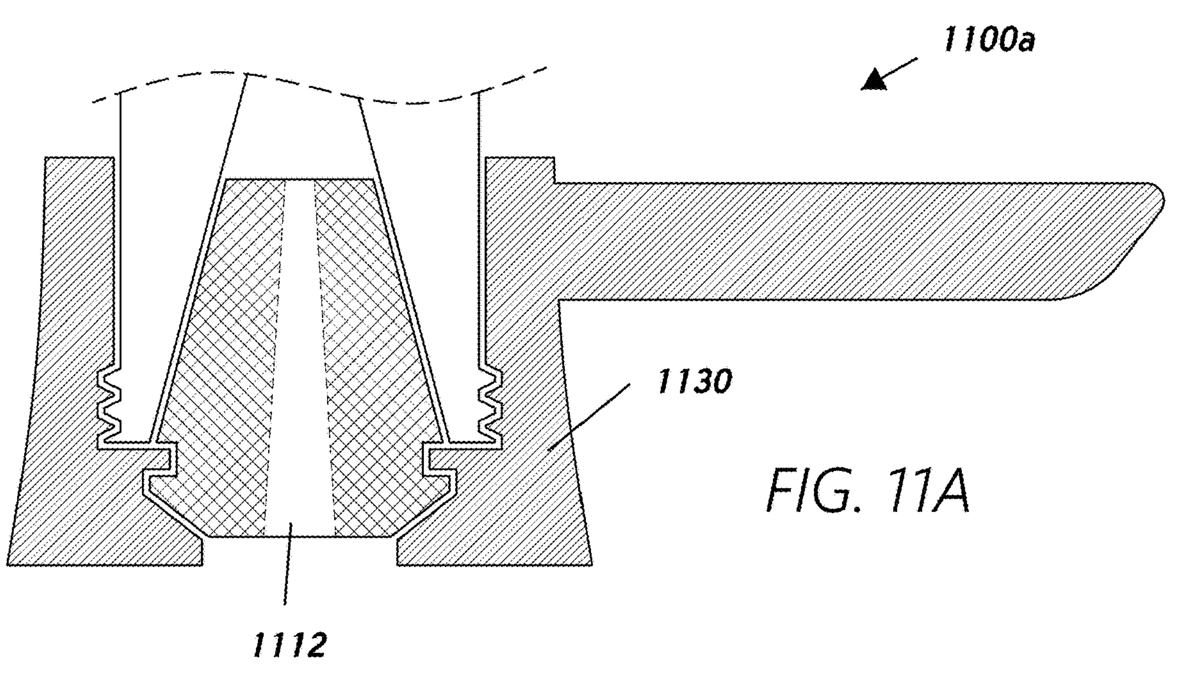
FIGS. 11A, 11B, 11C, and 11D illustrate other example connector assemblies that include a connector comprising a lever-actuated cam and a ball bearing locking mechanism.
Figure 11B:
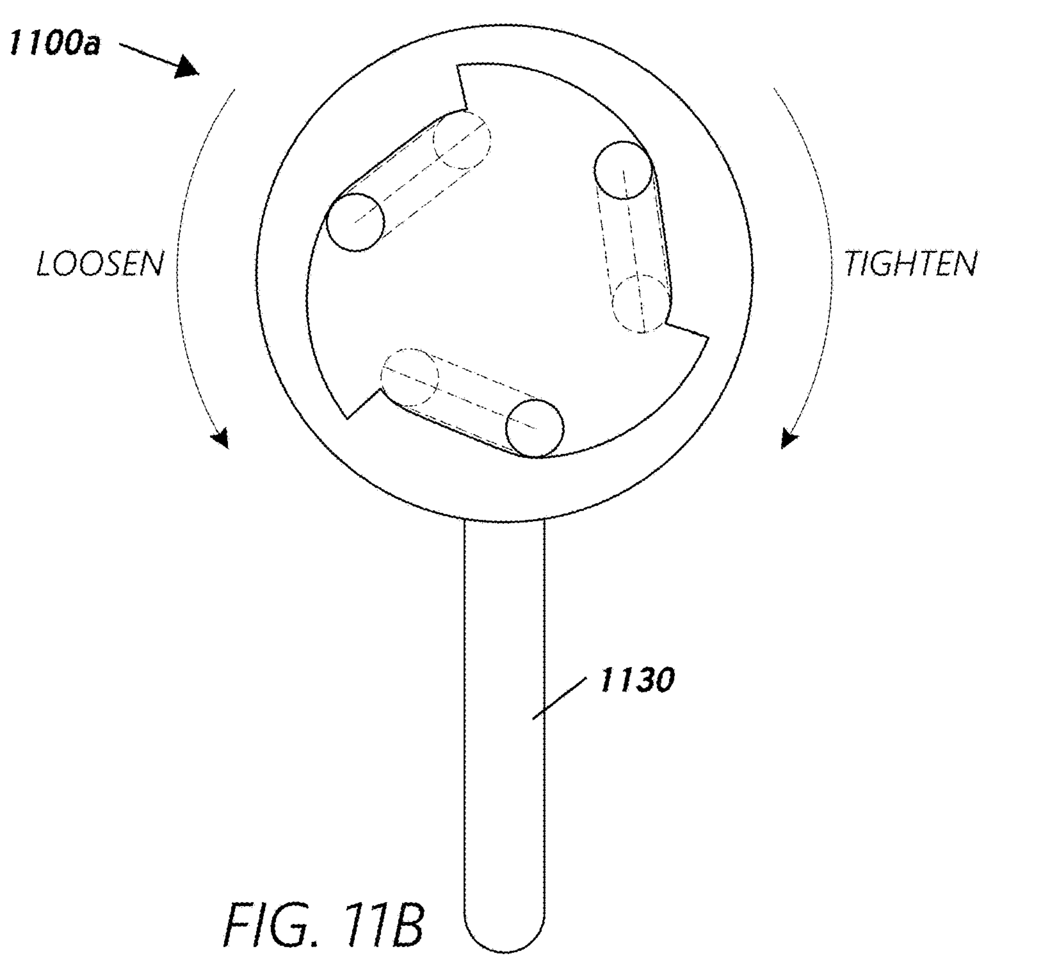
Figure 11C:
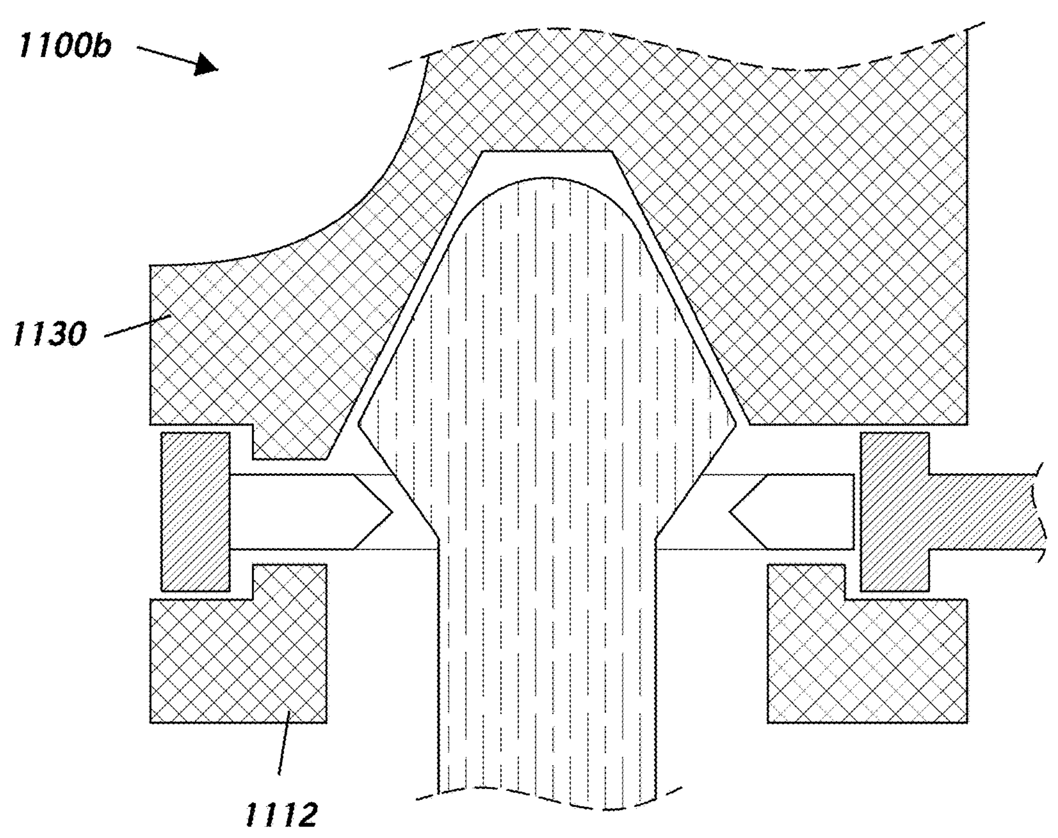
Figure 11D:
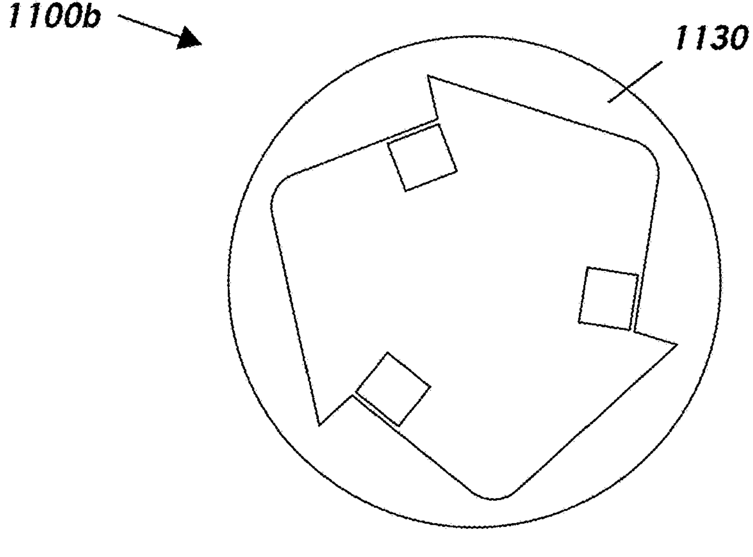

FIG. 10 shows another example connector assembly 1000 that includes a connector 1030 comprising a lever-actuated collet 1032 and a connector interface comprising a mating circular pin 1012. The tapered pin 1012 is configured to accommodate varying drape thicknesses. The lever-actuated collet 1032 can be placed over the pin 1012 and can accommodate the thickness of the surgical drape as it is placed over the pin 1012. The lever 1032 can be spring-loaded with a cam so that it is self-latching (e.g., the cam can be designed to mate with the tapered pin 1012 to self-latch). Actuating the lever 1032 drives the cup down over the tapered pin 1012. The pitch of the taper is such that it is low enough to self-lock from a fraction standpoint against the pin 1012.

FIGS. 11A-11D illustrate other example connector assemblies 1100*a*, 1100*b* that include a connector 1130 comprising a lever-actuated cam and a ball bearing locking mechanism. The ball bearings can interact directly with a locking pin 1112 or can have plungers that the ball bearings actuate to increase mechanical interlock. The connector assembly 1100*a* can utilize a collet. A shaft protrudes from the base and runs through the center of the collet. The lever rotates around and causes the ball bearings to tighten around the pin 1112 using ball bearings sitting on raceways. Rotation of the lever causes the ball bearings to move up the ramp, drawn in around the diameter, and the ball bearings are forced in on the groove of the pin 1112. The connector assembly 1100*b* replaces the ball bearings with profiled plungers to gain line contact with the pin 1112 rather than point contact provided by the ball bearings. The connector 1130 of the connector assembly 1100*b* uses geometry-driven cams to push a pin to the shaft.

Figure 12:
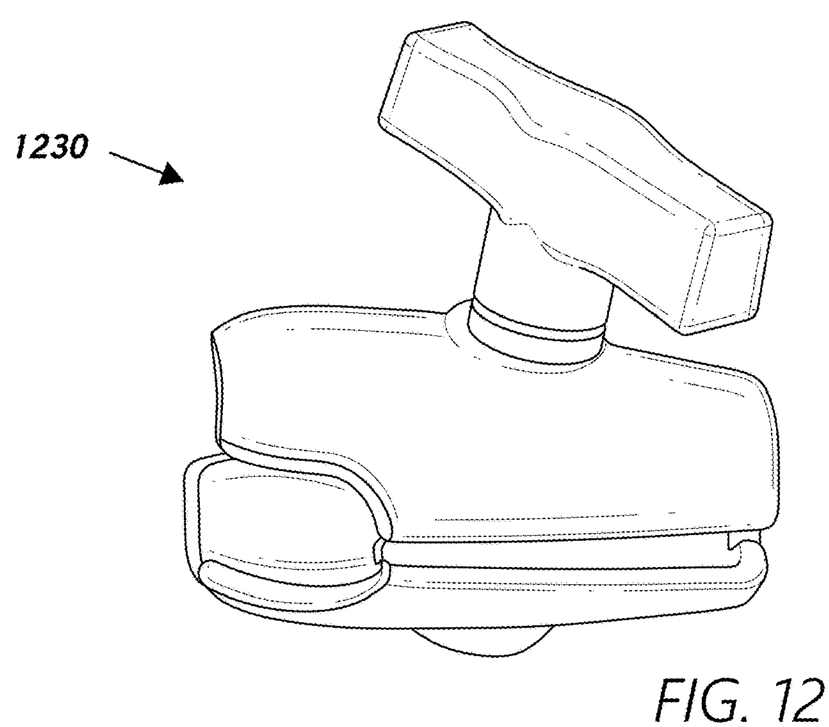
FIG. 12 illustrates another example connector that interfaces with a ball, similar to the ball of the connector assembly described herein with reference to FIGS. 7A and 7B.

FIG. 12 illustrates another example connector 1230 that interfaces with a ball, similar to the ball of the connector assembly 700 described herein with reference to FIGS. 7A and 7B. The connector 1230 comprises a screw-actuated lever to achieve the ball-hitch style connection. The connector 1230 is part of a ball and socket joint with a fulcrum between the socket on the bottom and the screw that is used to clamp the connector 1230 onto a ball extending from the base.

Figure 13:
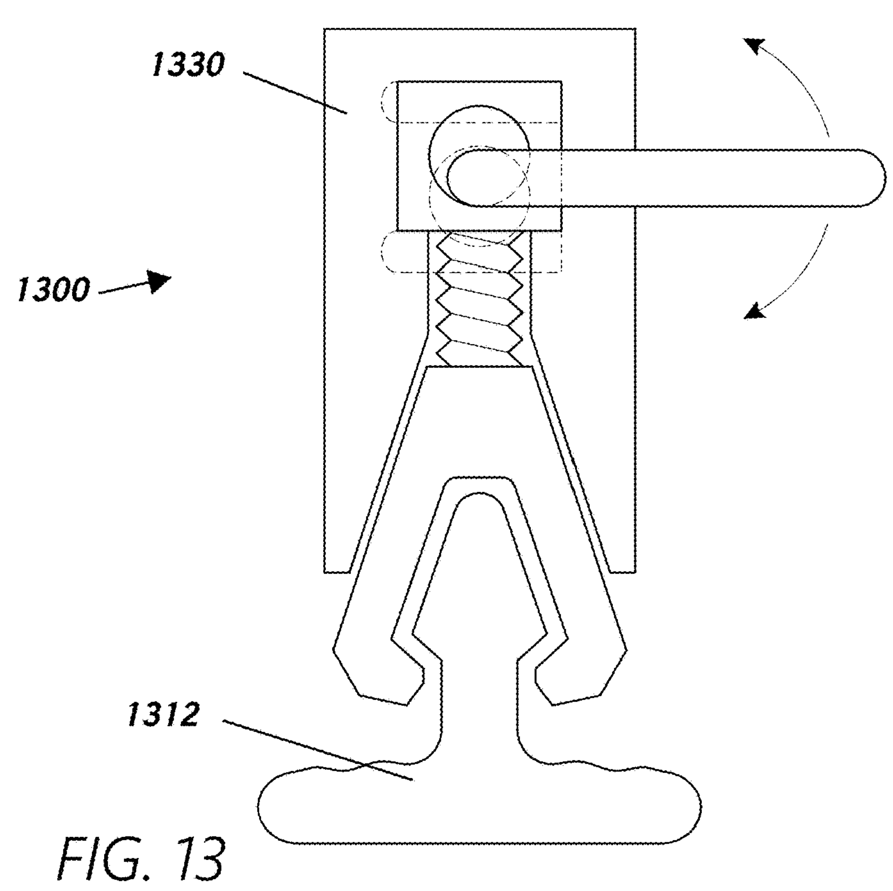
FIG. 13 illustrates another example connector assembly that includes a connector comprising a friction/cam-lock actuated collet and a connector interface comprising a pin compatible with the collet.

FIG. 13 illustrates another example connector assembly 1300 that includes a connector 1330 comprising a friction/cam-lock actuated collet and a connector interface comprising a pin 1312 compatible with the collet. The lever rotates and forces the threaded shaft up and down onto the tapered socket, closing the geometry around the tapered pin 1312. The connector 1330 functions similar to a collet.

Figure 14A:
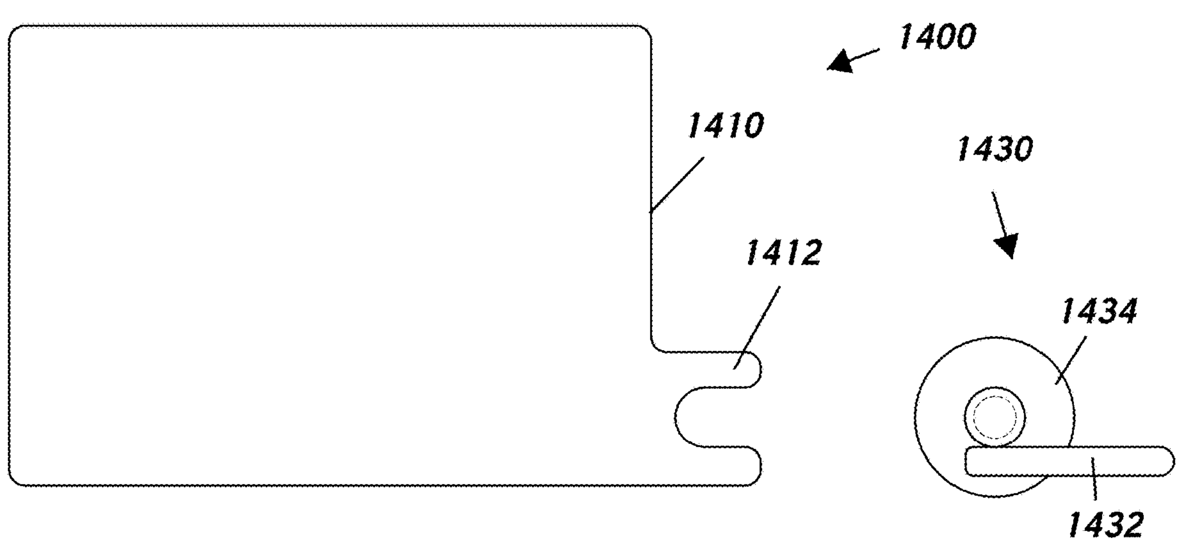
FIGS. 14A and 14B show another example connector assembly that includes a connector interface comprising a slotted portion of the base and a connector comprising a self-locking cam lever clamp.
Figure 14B:
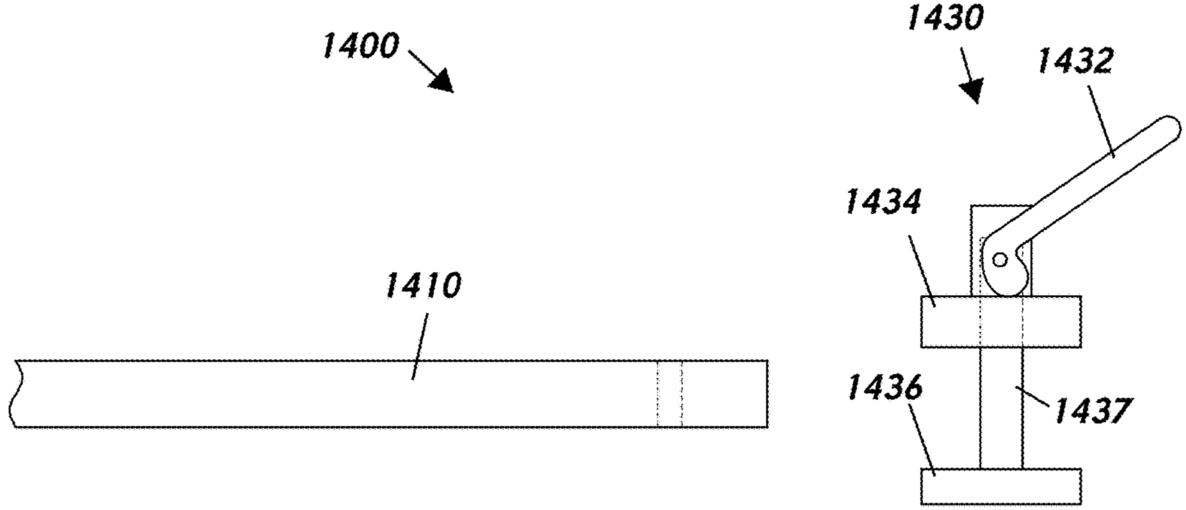

FIGS. 14A and 14B show another example connector assembly 1400 that includes a base mounting interface 1412 comprising a slotted portion of the base 1410 and a connector 1430 comprising a self-locking cam lever clamp. The base mounting interface 1412 is integrated into the base 1410 of a stabilizer system. The connector 1430 acts in a fashion similar to the connector 130 of FIGS. 1A-1C, wherein the lever 1432 is used to press a top clamp plate 1434 downward onto a round bottom plate 1436 over a shaft 1437 with the base mounting interface 1412 between the two plates 1434, 1436. The sterile drape can be positioned in the gap between the top plate 1434 and the bottom plate 1436 to maintain sterility. The lever 1432 can be part of a self-locking cam lever that locks the top plate 1434 in place. It is to be understood that the base mounting interface 1412 can be integral with the base 1410 or it can be separable from the base 1410.

ADDITIONAL FEATURES AND EMBODIMENTS

Although certain preferred embodiments and examples are disclosed herein, inventive subject matter extends beyond the specifically disclosed embodiments to other alternative embodiments and/or uses, and to modifications and equivalents thereof. Thus, the scope of the claims that may arise herefrom is not limited by any of the particular embodiments described herein. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. The description of embodiments of the disclosure is not intended to be exhaustive or to limit the disclosure to the precise forms disclosed herein. While specific embodiments, and examples, are described above for illustrative purposes, various equivalent modifications are possible within the scope of the disclosure, as those skilled in the relevant art will recognize.

Certain terms of location are used herein with respect to the various disclosed embodiments. Although certain spatially relative terms, such as "outer," "inner," "upper," "lower," "below," "above," "vertical," "horizontal," "top," "bottom," and similar terms are used herein to describe a spatial relationship of one device/element or anatomical structure relative to another device/element or anatomical structure, it is understood that these terms are used herein for case of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited. In some contexts, description of an operation or event as occurring or being performed "based on," or "based at least in part on," a stated event or condition can be interpreted as being triggered by or performed in response to the stated event or condition.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

Unless the context clearly requires otherwise, throughout the description and the claims, the terms "comprise," "comprising," "have," "having," "include," "including," and the like are to be construed in an open and inclusive sense, as opposed to a closed, exclusive, or exhaustive sense; that is to say, in the sense of "including, but not limited to."

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

The word "coupled", as generally used herein, refers to two or more elements that may be physically, mechanically, and/or electrically connected or otherwise associated, whether directly or indirectly (e.g., via one or more intermediate elements, components, and/or devices. Additionally, the words "herein," "above," "below," and words of similar import, when used in this application, shall refer to this application as a whole, including any disclosure incorporated by reference, and not to any particular portions of the present disclosure. Where the context permits, words in present disclosure using the singular or plural number may also include the plural or singular number, respectively.

The word "or" in reference to a list of two or more items, that word covers all of the following interpretations of the word: any of the items in the list, all of the items in the list, and any combination of the items in the list. Furthermore, as used herein, the term "and/or" used between elements (e.g., between the last two of a list of elements) means any one or more of the referenced/related elements. For example, the phrase "A, B, and/or C" means "A," "B," "C," "A and B," "A and C," "B and C," or "A, B, and C."

As may be used herein, the terms "substantially" and "approximately" provides an industry-accepted tolerance for its corresponding term and/or relativity between items. For some industries, an industry-accepted tolerance is less than one percent, while for other industries, the industry-accepted tolerance may be 10 percent or more. Other examples of industry-accepted tolerances range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than approximately +/−1%). Some relativity between items may range from a difference of less than a percentage level to a few percent. Other relativity between items may range from a difference of a few percent to magnitude of differences.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same, related, or unrelated reference numbers. The relevant features, elements, functions, operations, modules, etc. may be the same or similar functions or may be unrelated.

What is claimed is:

1. A stabilizer system for use in a medical procedure to stabilize an access sheath or a delivery device, the stabilizer system comprising:

a base configured to be positioned between a patient table and a pad on the patient table;

an articulating arm;

a connector configured to secure the articulating arm to a portion of the base that protrudes from under the pad; and a holder at a distal end of the articulating arm, the holder configured to interface with the access sheath or delivery device, wherein the connector is configured to connect to the base in a way that maintains sterility of the articulating arm above a sterile barrier during connection of the connector to the base, wherein the base includes a stabilizing portion and a protruding portion separated by a wall that extends vertically from the base.

2. The stabilizer system of claim 1, wherein the portion of the base that protrudes from under the pad forms a base mounting portion that mates with the connector.

3. The stabilizer system of claim 1, wherein the connector comprises an arm mating pin configured to mate with the articulating arm.

4. The stabilizer system of claim 1, wherein the connector comprises a shaft, a tapered clamp plate, and a bottom clamp plate.

5. The stabilizer system of claim 4, wherein the tapered clamp plate has an oblong cross-section.

6. The stabilizer system of claim 5, wherein the base forms a base mounting portion with an oblong shape complementary to the oblong cross-section of the tapered clamp plate.

7. The stabilizer system of claim 4, wherein the base forms a base mounting portion that is tapered to complement a taper of the tapered clamp plate.

8. The stabilizer system of claim 4, wherein the connector connects to the base by applying a clamping force on the base between the tapered clamp plate and the bottom clamp plate.

9. The stabilizer system of claim 1, wherein the base forms a base mounting portion on the portion of the base that protrudes from under the pad.

10. The stabilizer system of claim 9, wherein a surgical drape is configured to lie between the base mounting portion and the connector upon connecting the connector to the base.

11. The stabilizer system of claim 1, wherein the base is radiolucent.

12. The stabilizer system of claim 1, wherein the articulating arm comprises a vertical post that is held vertically stable in relation to the connector during a medical procedure.

13. The stabilizer system of claim 1, wherein the holder is releasably attached to the articulating arm.

14. The stabilizer system of claim 1, wherein the articulating arm is releasably attached to the connector.

15. A stabilizer system comprising:

a base comprising a stabilizing portion and a protruding portion, the stabilizing portion configured to be inserted between a mattress and a table such that the protruding portion extends outward from between the mattress and the table, the protruding portion forming a base mounting portion; and a connector comprising a shaft, a top plate, and a bottom plate, the top plate and the bottom plate configured to approximate to each other along an axial direction of the shaft, wherein the connector is configured to mate with the base mounting portion to secure the connector to the base with a surgical drape pressed between the connector and the base, the top plate and the bottom plate configured to apply a clamping force on the base mounting portion to secure the connector to the base.

16. The stabilizer system of claim 15 further comprising a knob coupled to the top plate, wherein rotation of the knob causes the top plate and the bottom plate to axially approximate.

17. The stabilizer system of claim 16, wherein the connector further includes a grooved ring assembly to secure the knob to the top plate such that rotation of the knob causes the top plate to translate axially along the shaft toward the bottom plate.

18. The stabilizer system of claim 15, wherein the top plate is internally keyed to a cross-section of the shaft to prohibit rotation of the top plate relative to the shaft.

19. A stabilizer system for use in a medical procedure to stabilize an access sheath or a delivery device, the stabilizer system comprising:

a base configured to be positioned between a patient table and a pad on the patient table;

an articulating arm;

a connector configured to secure the articulating arm to a portion of the base that protrudes from under the pad; and a holder at a distal end of the articulating arm, the holder configured to interface with the access sheath or delivery device, wherein the connector is configured to connect to the base in a way that maintains sterility of the articulating arm above a sterile barrier during connection of the connector to the base, wherein the holder comprises a lever-actuated clamp with pre-tensioned springs to form a two-stage clamping mechanism.

* * * * *